US010844367B2

(12) United States Patent
Nicolas et al.

(10) Patent No.: US 10,844,367 B2
(45) Date of Patent: Nov. 24, 2020

(54) YEAST STRAIN IMPROVEMENT METHOD

(71) Applicants: INSTITUT CURIE, Paris (FR); CENTRE NATIONAL DE LA RECHERCHE SCIENTIFIQUE, Paris (FR); UNIVERSITE PIERRE ET MARIE CURIE (PARIS 6), Paris (FR); UNIVERSITE NICE SOPHIA ANTIPOLIS, Nice (FR); INSERM (INSTITUT NATIONAL DE LA SANTE ET DE LA RECHERCHE MEDICALE), Paris (FR)

(72) Inventors: Alain Nicolas, Paris (FR); Gianni Liti, Nice (FR)

(73) Assignees: INSTITUT CURIE, Paris (FR); CENTRE NATIONAL DE LA RECHERCHE SCIENTIFIQUE, Paris (FR); UNIVERSITE PIERRE ET MARIE CURIE (PARIS 6), Paris (FR); UNIVERSITE NICE SOPHIA ANTIPOLIS, Nice (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 650 days.

(21) Appl. No.: 14/647,858

(22) PCT Filed: Nov. 29, 2013

(86) PCT No.: PCT/EP2013/075045
§ 371 (c)(1),
(2) Date: May 28, 2015

(87) PCT Pub. No.: WO2014/083142
PCT Pub. Date: Jun. 5, 2014

(65) Prior Publication Data
US 2015/0307868 A1 Oct. 29, 2015

(30) Foreign Application Priority Data

Nov. 30, 2012 (FR) .................................. 12 61456

(51) Int. Cl.
*C12N 15/01* (2006.01)
*C12N 15/81* (2006.01)
*C12N 1/16* (2006.01)
*C12N 1/18* (2006.01)
*C12N 1/36* (2006.01)
*C12N 9/90* (2006.01)
*C12Q 1/6895* (2018.01)

(52) U.S. Cl.
CPC ............... *C12N 15/01* (2013.01); *C12N 1/16* (2013.01); *C12N 1/18* (2013.01); *C12N 1/36* (2013.01); *C12N 9/90* (2013.01); *C12Q 1/6895* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

2004/0033494 A1   2/2004   Nicolas et al.

FOREIGN PATENT DOCUMENTS

JP        H 11313668        11/1999

OTHER PUBLICATIONS

Esposito, R.E., et al., "Genetic Recombination and Commitment to Meiosis in *Saccharomyces*," *Proceedings of the National Academy of Sciences*, Aug. 1974, vol. 71, No. 8, pp. 3172-3176.
Sherman, F., et al., "Evidence for Two Types of Allelic Recombination in Yeast," *Genetics*, Feb. 1963, vol. 48, pp. 255-261.
Zenvirth, D., et al., "Switching yeast from meiosis to mitosis: double-strand break repair, recombination and synaptonemal complex," *Genes to Cells*, Aug. 1, 1997, vol. 2, No. 8, pp. 487-498.
Fischer, G. et al. "Chromosomal evolution in *Saccharomyces*" *Nature*, May 25, 2000, pp. 451-454, vol. 405.

*Primary Examiner* — Channing S Mahatan
(74) *Attorney, Agent, or Firm* — Saliwanchik, Lloyd & Eisenschenk

(57) ABSTRACT

The present invention relates to a method for improving an industrial yeast strain of industrial interest, particularly a sterile hybrid strain, without resorting to recombinant DNA techniques.

16 Claims, 19 Drawing Sheets

Specification includes a Sequence Listing.

YEAST STRAIN IMPROVEMENT METHOD

CROSS-REFERENCE TO RELATED APPLICATION

This application is the U.S. national stage application of International Patent Application No. PCT/EP2013/075045, filed Nov. 29, 2013.

The Sequence Listing for this application is labeled "Seq-List.txt" which was created on May 11, 2015 and is 1 KB. The entire contents of the sequence listing is incorporated herein by reference in its entirety.

The present invention relates to the field of microbiology, particularly the field of yeasts. It especially relates to a method for improving or modifying a yeast strain of industrial interest, particularly a hybrid strain unable to sporulate, without resorting to recombinant DNA techniques.

BACKGROUND OF THE INVENTION

Yeasts are used in a wide variety of industries. Due to the harmlessness of a large number of species, yeasts are especially used in the food industry as a fermentation agent in baking, brewing, winemaking, or distilling, or as extracts for nutritional elements or flavorings. They may also be used in the industrial production of bioethanol or useful molecules such as vitamins, antibiotics, vaccines, enzymes, or steroid hormones, or even in cellulosic material degradation processes.

The diversity of the industrial applications of yeast, especially *Saccharomyces cerevisiae*, means that there is a constant demand for yeast strains having improved characteristics, or at least that are suitable for a new usage or new culture conditions.

A person skilled in the art has a variety of tools and methods available for obtaining a strain having a specific characteristic. In particular, he can genetically modify the strain by introducing one or more heterologous genes while modifying or eliminating the expression of endogenous genes. However, using a recombinant DNA technique to genetically modify a strain can restrict its use industrially due to regulatory, health, or environmental factors.

Sexual reproduction can also be used to improve yeasts, by crossing two parental strains having characteristics of interest and selecting a hybrid strain providing the desired combination of parental characteristics. Haploid cells from products of sporulation can be screened to identify those in which meiotic recombination yielded the desired characteristic.

However, the yeast strains used in industry are often hybrid cells obtained by crossing genetically distinct strains and may be sterile because of their inability to produce viable spores. For these hybrid cells which are of major economic interest, it is impossible to generate genetic diversity through sexual reproduction and screening of sporulation products.

SUMMARY OF THE INVENTION

The aim of the present invention is to provide a novel method for improving yeast strains of industrial interest, including sterile hybrid yeasts, without resorting to recombinant DNA techniques, and to obtain yeasts, preferably with a ploidy level greater than or equal to 2, and in particular diploid, of a recombinant genotype allowing rapid analysis of quantitative traits of interest.

According to a first aspect, the invention therefore relates to a method for improving a yeast strain of industrial interest, comprising:

a) transferring the yeast from a rich medium to a sporulation medium, preferably having no source of fermentable carbon or nitrogen;

b) incubating the yeasts in the sporulation medium for a length of time sufficient to induce the formation of Spo11-dependent double-strand breaks;

c) placing the yeasts in contact with a source of carbon and nitrogen before the reductional chromosome segregation of the first meiotic division in order to obtain recombinant yeasts;

d) collecting the recombinant yeasts; and e) screening or selection of the recombinant yeasts in order to identify those having the desired improvement.

The method may further include obtaining one or more recombinant yeasts having the desired improvement, from the screening or selection of step e).

It also relates to using the yeast RTG process to improve a yeast strain of industrial interest, said RTG process being induced by transferring the yeast from a rich medium to a sporulation medium, preferably having no source of fermentable carbon or nitrogen, incubating the yeasts in the sporulation medium for a length of time sufficient to induce the formation of Spo11-dependent double-strand breaks, and placing the yeasts in contact with a source of carbon and nitrogen before the reductional chromosome segregation of the first meiotic division.

Preferably, the yeast of industrial interest has a ploidy level that is greater than or equal to 2.

The yeast strain of industrial interest may be a hybrid yeast.

It may be haploid, aneuploid, diploid, or polyploid, preferably diploid, aneuploid, or polyploid, and more preferably diploid.

Preferably, the yeast of industrial interest is a diploid hybrid yeast.

The yeast strain of industrial interest may be a sterile yeast, preferably a sterile hybrid strain.

In a preferred embodiment, the yeast strain of industrial interest is a sterile diploid hybrid strain.

In a preferred embodiment, the strain is a non-genetically modified organism.

The recombinant yeasts present one or more recombination events per cell, preferably a plurality of recombination events. Preferably, said recombination events induce a decrease in the level of heterozygosity.

A nucleic acid encoding a fusion protein, under the control of a promoter, preferably meiosis-specific, comprising a DNA-binding domain operably linked to a Spo11 protein or to a partner protein of Spo11, can be introduced into the strain of industrial interest to locally increase the frequency of double-strand breaks in the meiotic prophase or to modify the distribution of such breaks along the chromosomes.

Steps a) to d) or a) to e) may be repeated at least once using one or more recombinant yeasts.

The recombinant yeasts collected in step d) may be stored in yeast libraries before the screening or selection of step e).

Preferably, the recombinant or improved yeasts obtained by the method of the invention are not genetically modified organisms (GMOs).

The yeast strain of industrial interest is preferably intended for the food industry, for the production of biofuel, particularly bioethanol, for the production of useful molecules such as vitamins, antibiotics, vaccines, enzymes, or steroid hormones, or for the degradation of cellulose or lignocellulosic biomass, and/or is preferably of the species *Saccharomyces cerevisiae* or is a hybrid obtained from *Saccharomyces cerevisiae*.

The desired improvement may concern one or more characteristics selected from the group consisting of growth rate, thermotolerance, cryotolerance, pH sensitivity, fermentability, fermentation rate, resistance to ethanol, resistance to a particular compound present in the fermentation medium or excreted from the cell culture, cell morphology, flocculation, sensitivity to a particular molecule, efficiency of sporulation, aromatic profiles, nutritional requirements, resistance to drying, and fermentation of a particular sugar.

According to a second aspect, the invention relates to a method for generating a recombinant yeast library from a yeast, comprising:

a) transferring the yeast from a rich medium to a sporulation medium, preferably having no source of fermentable carbon or nitrogen;

b) incubating the yeasts in the sporulation medium for a length of time sufficient to induce Spo11-dependent double-strand breaks:

c) placing the yeasts in contact with a source of carbon and nitrogen before the reductional chromosome segregation of the first meiotic division in order to obtain recombinant yeasts; and d) collecting the recombinant yeasts in order to form a recombinant yeast library.

The yeast may be haploid, aneuploid, diploid, or polyploid; preferably diploid, aneuploid, or polyploid; and more preferably diploid.

Preferably, the yeast has a ploidy level greater than or equal to 2.

It also relates to a library of recombinant yeasts obtained according to said method.

In another aspect, it also relates to a method for identifying or locating in a yeast the genetic information encoding a characteristic of interest, preferably a quantitative trait of interest (QTL), preferably a yeast having a ploidy level greater than or equal to 2, comprising:

a) transferring the yeast from a rich medium to a sporulation medium, preferably having no source of fermentable carbon or nitrogen;

b) incubating the yeasts in the sporulation medium for a length of time sufficient to induce Spo11-dependent double-strand breaks;

c) placing the yeast in contact with a source of carbon and nitrogen before the reductional chromosome segregation of the first meiotic division in order to obtain recombinant yeasts;

d) collecting the recombinant yeasts; and e) analyzing the genotypes and phenotypes of the recombinant yeasts to identify or locate the genetic information encoding the characteristic of interest.

In particular, the characteristic of interest can be selected from the group consisting of growth rate, thermotolerance, cryotolerance, pH sensitivity, fermentability, fermentation rate, resistance to ethanol, resistance to a particular compound present in the fermentation medium or excreted from the cell culture, cell morphology, flocculation, sensitivity to a particular molecule, efficiency of sporulation, aromatic profiles, nutritional requirements, resistance to drying, and fermentation of a particular sugar.

BRIEF DESCRIPTION OF DRAWINGS

FIG. 1: Maps of SNPs in RTG cells obtained by "return-to-growth" protocol 2, meaning by depositing the cells collected during sporulation on an arginine dropout selective medium in order to select the recombinant cells carrying an ARG4 allele. The genotype of the two homologous chromosomes is shown for each RTG diploid: heteroallelic (light gray), monoallelic (dark gray) if the origin is SK1 or monoallelic (black) if the origin is S288C.

FIG. 2: Maps of SNPs in mother/daughter pairs issuing from "return-to-growth" protocol 3, meaning by isolation of RTG cells by micromanipulation. For each RTG diploid, the mother and daughter cells from the same RTG event are grouped.

Figure 4:
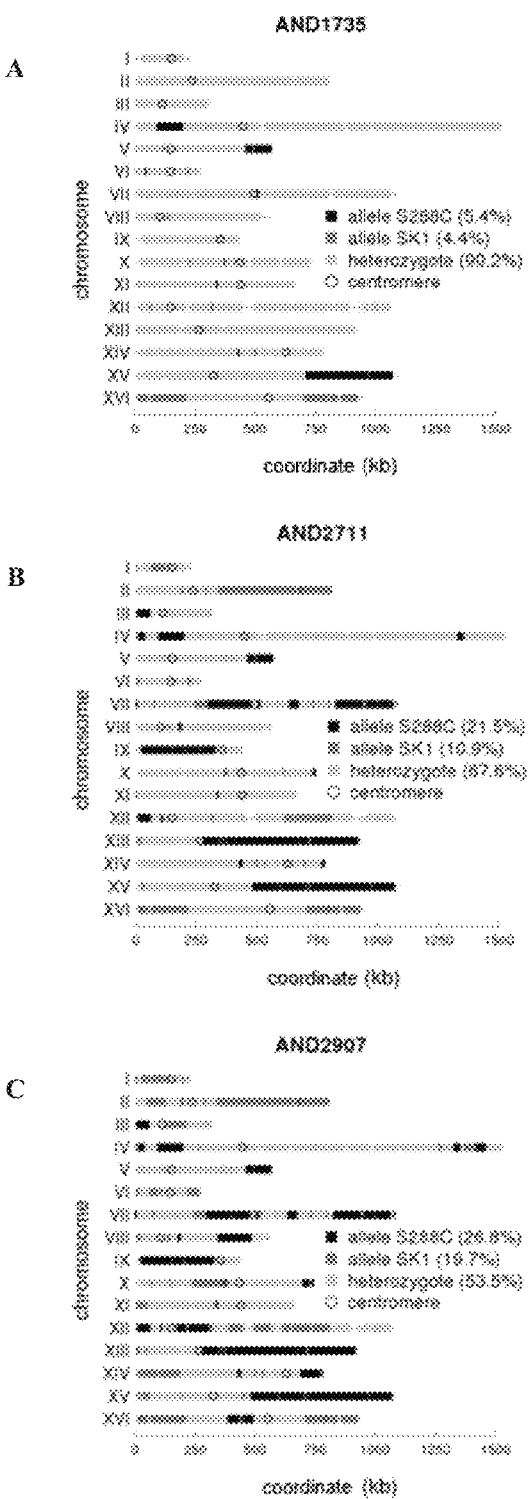
FIG. 4. Maps of SNPs of cells issuing from repeating the RTG process. The AND1735 RTG cell (FIG. 2B and FIG.

4A) has undergone a second RTG cycle generating recombinant diploid cell AND2711 (FIG. 4B) and then a third RTG cycle generating recombinant diploid cell AND2907 (FIG. 4C). The percentage of heterozygosity and the relative percentage of alleles of S288C or SK genetic background calculated from the regions of loss of heterozygosity are shown (FIGS. 4A-C). Repeating the RTG process leads to additional recombinants, a gradual decrease in the level of heterozygosity, and variations in the proportion of monoallelic regions of purely S288C and SK1 genotype (FIGS. 4A-C).

Figure 5A:
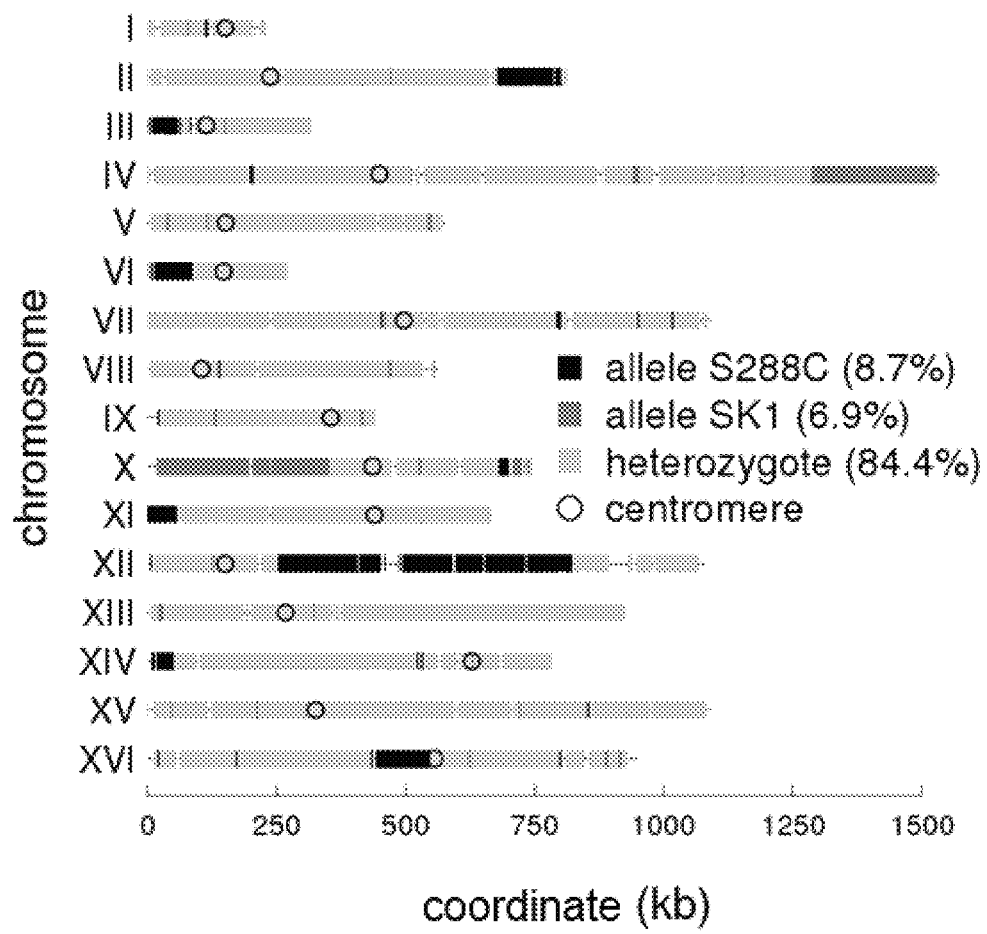
Figure 5B:
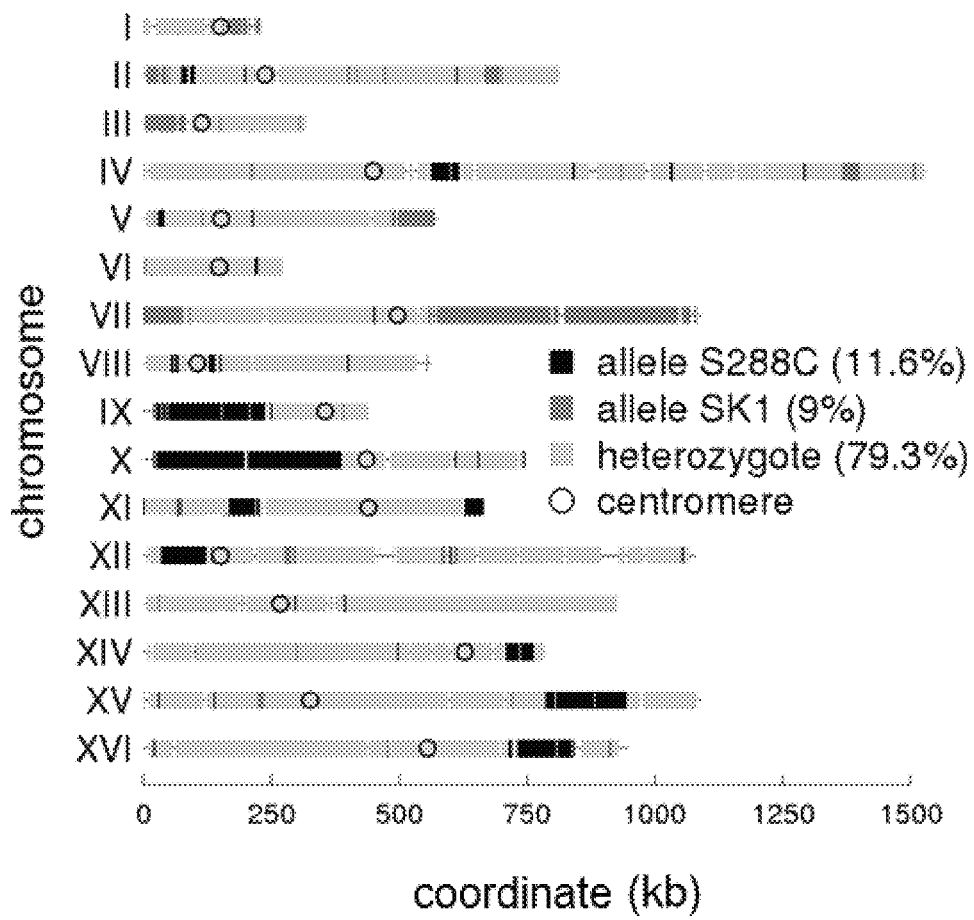
Figure 5C:
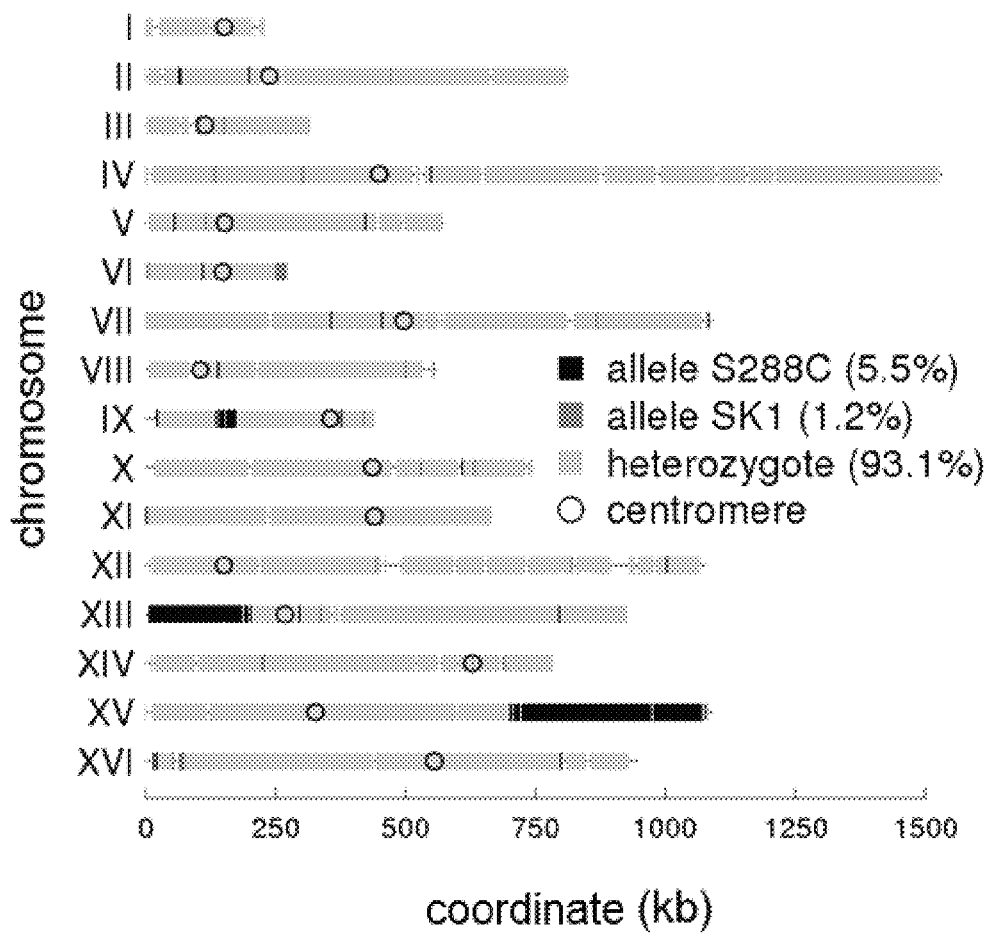

FIG. 5. Maps of SNPs of RTG cells issuing from the AND2248 sporulation-deficient strain. These three cells, AND2642 (FIG. 5A), AND2652 (FIG. 5B), and AND2658 (FIG. 5C), issuing from an RTG cycle are diploid and of recombinant genotype. Their genotype is different. In all three cases, the level of heterozygosity is reduced relative to the parental cell (84.4%, 79.3%, and 93.1%), and S288C or SK1 monoallelic regions appeared in variable proportions.

Figure 6:
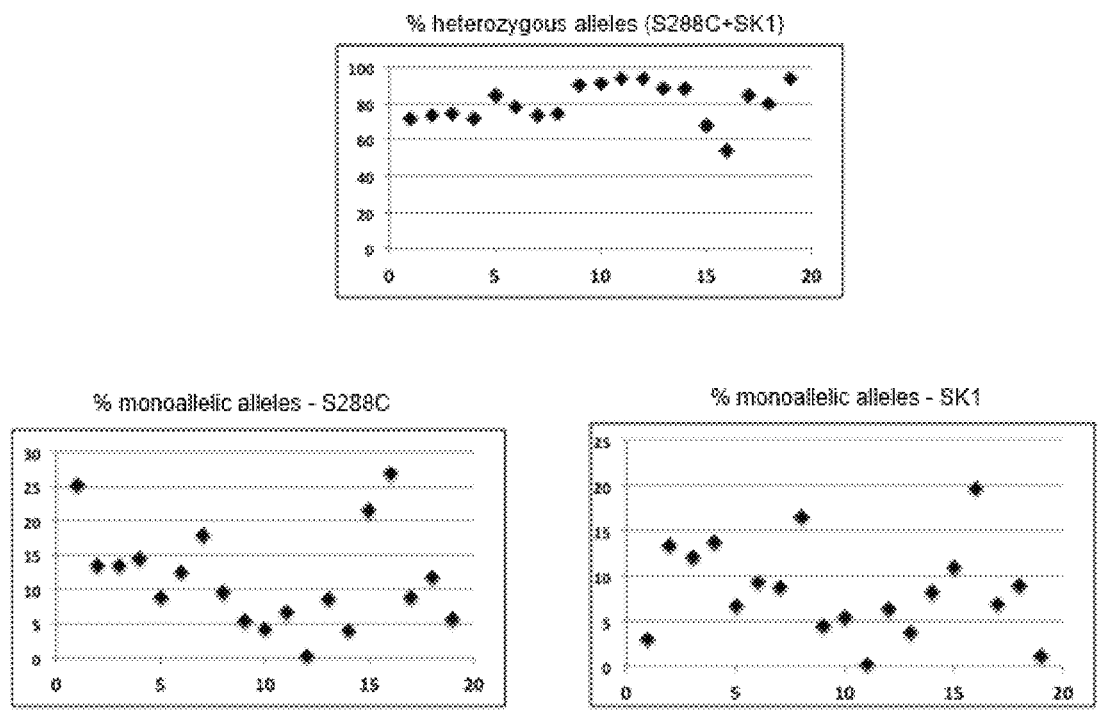

FIG. 6. Comparative analysis of allelic genotype of 19 RTG cells issuing from diploid cells AND1702, AND1735, AND2907, and AND2248. For each RTG cell, the figure shows the percentage of SNPs that are biallelic (heterozygous), monoallelic if originating from 288C, or monoallelic if originating from SK1. Their proportions vary from one RTG cell to another.

Figure 7A:
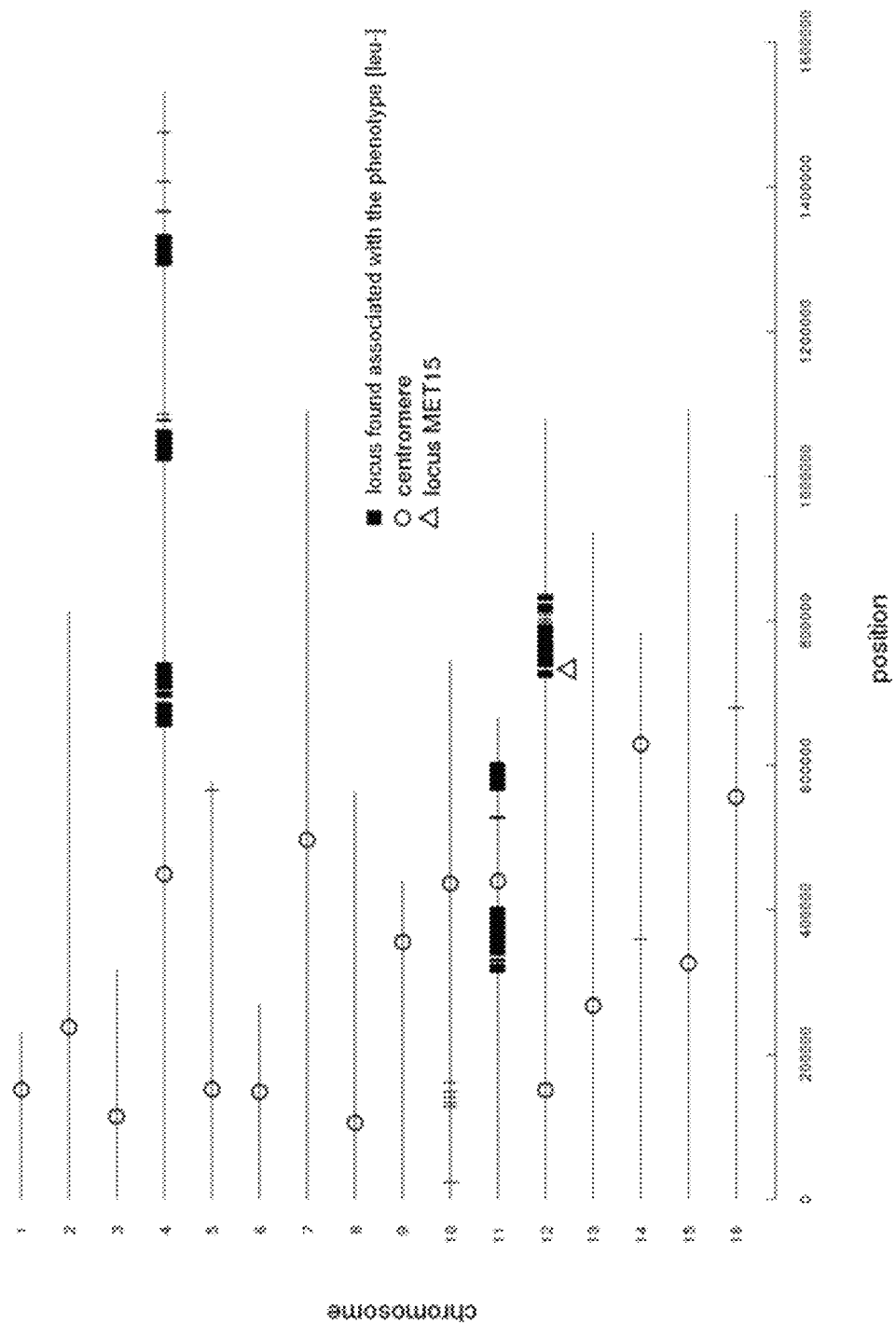
Figure 7B:
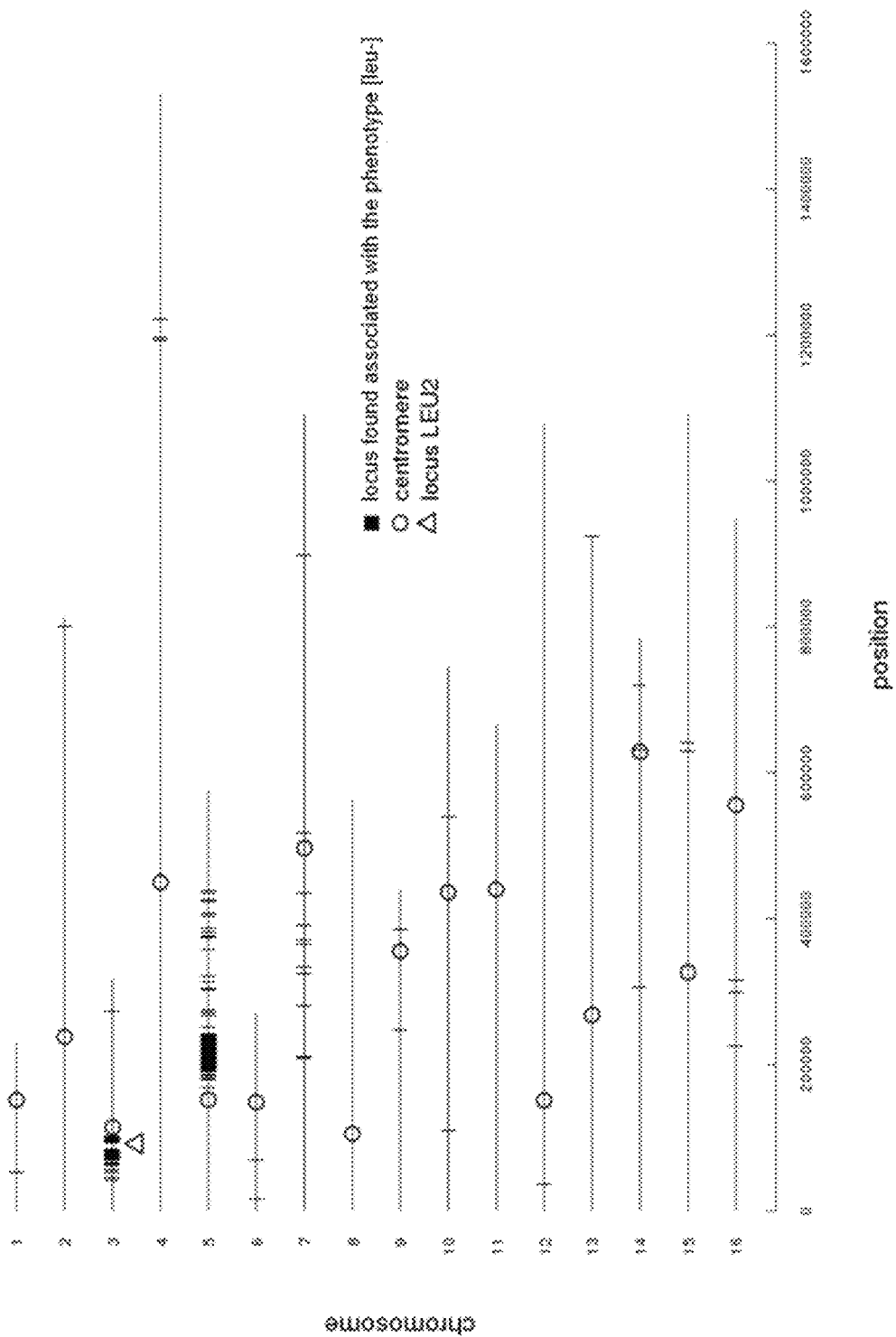

FIG. 7. Maps of positions of SNP polymorphism associated with simple phenotypes. The length of each chromosome is represented by a thin horizontal black line. Studying several cells issuing from RTG has the effect of reducing the number of candidate regions and improving the resolution of the map in the remaining regions. Due to the low number of samples analyzed, several candidate regions are associated with the auxotrophic phenotype for methionine or leucine. FIG. 7A: Map of positions of SNP associated with the auxotrophic phenotype for methionine. The locus MET15 (triangle) is associated with the auxotrophic phenotype for methionine. FIG. 7B: Map of positions of SNP polymorphism associated with the auxotrophic phenotype for leucine. The locus LEU2 (triangle) is associated with the auxotrophic phenotype for leucine.

Figure 8:
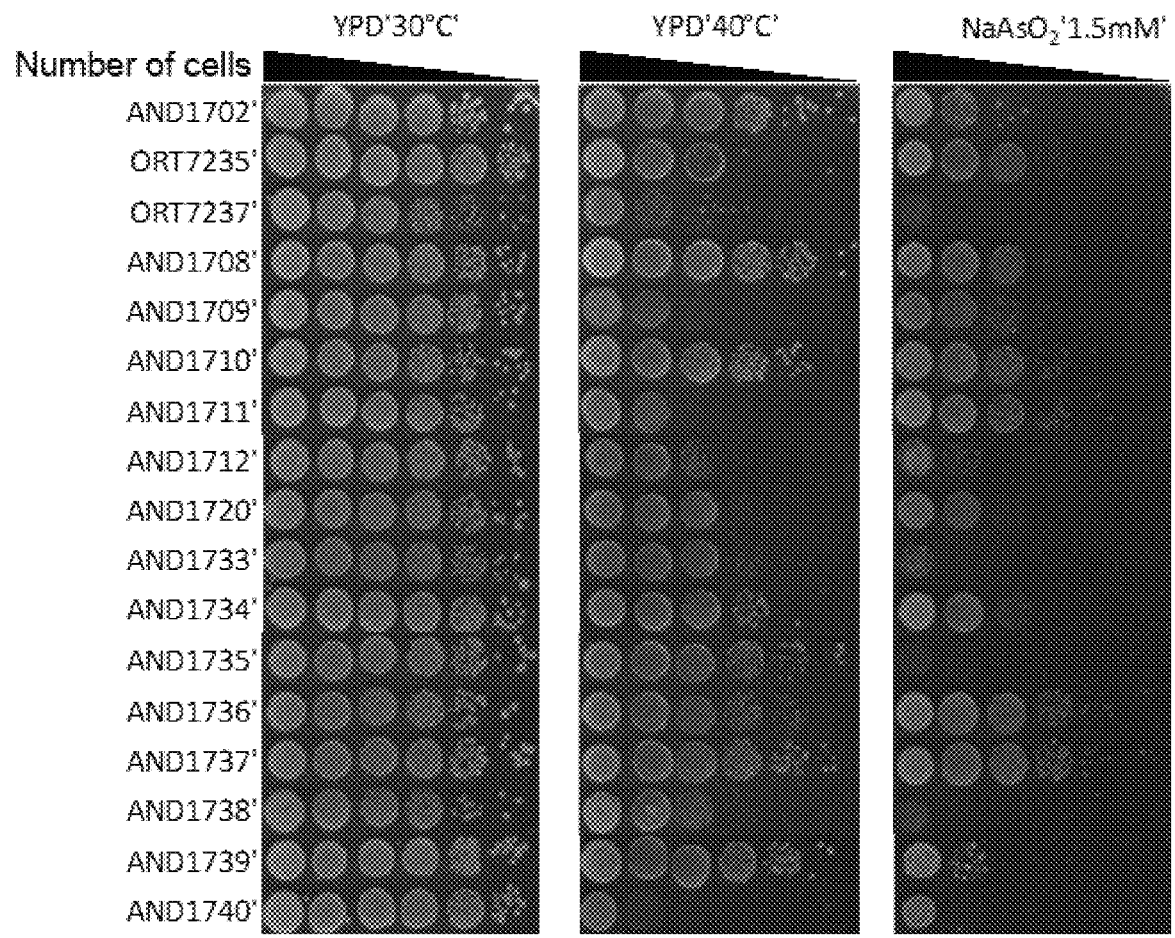

FIG. 8. Growth tests for RTG and parental cells. Growth at 30° C., 40° C. on YPD medium and at 30° C. on YPD medium containing sodium arsenite (1.5 mM $NaAsO_2$). For each strain, $10^6$, $10^5$, $10^4$, $10^3$, $10^2$, and $10^1$ cells were deposited on YPD medium and incubated 2 days at 30° C. with and without $NaAsO_2$ or at 40° C. (without $NaAsO_2$).

DETAILED DESCRIPTION OF THE INVENTION

Among the various species of yeast used in industry, Saccharomyces cerevisiae is quite common. S cerevisiae is a diplohaplontic unicellular eukaryotic organism, meaning it is an organism having a reproductive cycle in which cell multiplication occurs in both a haploid and a diploid state.

The cells can reproduce clonally by mitotic divisions. The daughter cell appears as a bud beginning in the S phase of genome replication, then grows and separates from the mother cell. During mitotic divisions, the entire genome (12,071,326 nucleotides for the nuclear genome) is replicated and accurately transmitted from mother cell to daughter cell. Homologous recombination phenomena may exist but are essentially for the repair of accidental double-strand breaks that can occur in the DNA when replication is blocked or cells are exposed to genotoxic agents. In this case, the sister chromatid is preferably used as matrix. During mitosis, recombination between homologous chromosomes rarely occurs which allows cells in vegetative growth to maintain the same gene pool.

Yeast can also reproduce by sexual reproduction through meiosis and sporulation. On the one hand, two haploid cells of opposite mating types (MATa and MATα) can fuse to form a diploid MATa/MATα cell which undergoes identical reproduction by mitosis. On the other hand, under conditions of nutrient deficiency, diploid cells enter sporulation through a meiotic process that generates four haploid spores, packaged in a tetrad, for each diploid cell. Germination of these spores produces haploid cells that are able to fuse to form a new diploid cell.

Initiation of the meiotic cycle depends on a number of signals transmitted simultaneously to the cell: a genetic signal of diploidy indicated by the presence of two mating alleles MATa and MATα, and nutrient signals indicating the absence of a source of nitrogen and fermentable carbon and the presence of a source of carbon that can be metabolized by respiration (Honigberg and Purnapatre, 2003).

During meiosis, unlike what occurs in mitotic divisions, genetic information from the diploid parental cells is not identically transmitted to the haploid cells. In fact, it is reduced by half and many genetic exchanges between homologous chromosomes occur during meiotic prophase I. The meiotic recombination which occurs during prophase I involves (i) formation of double-strand breaks by the Spo11 protein, (ii) excision of nucleotides at the 5' end of the breaks, (iii) invasion of the 3' protruding end of a strand at a chromatid of the homologous chromosome, and (iv) repair of the break producing a crossover (reciprocal exchange between homologous chromosomes), a gene conversion (copy of a DNA segment with no reciprocal exchange between homologous chromosomes), or both (gene conversion associated with crossover).

A distinctive feature of the yeast S. cerevisiae is that the induction of entry into meiotic prophase I is reversible. This process, called "Return to Growth" (RTG), occurs when diploid cells that have entered meiosis in response to a nutrient deficiency are placed in the presence of a source of carbon and nitrogen after the formation of Spo11-dependent double-strand breaks but before the first meiotic division (Honigberg and Esposito, 1994). Under these conditions, they stop progressing through the stages of meiotic differentiation to resume a mitotic growth mode while inducing recombinations during repair of the double-strand breaks caused by Spo11 (Sherman and Roman, 1963; Esposito and Esposito, 1974; Zenvirth et al., 1997). During the RTG process, it has been observed that double-strand breaks are repaired very quickly after the cells are transferred to a rich medium (Zenvirth et al., 1997). Although the mechanisms involved in these repairs have not yet been defined, it has been shown that they are distinct from those occurring during meiosis and seem to minimize crossover in order to preserve the integrity of the genome and limit loss of heterozygosity (Dayani et al., 2011).

In order to establish accurate maps of the genetic exchanges between homologous chromosomes during the RTG process, the inventors have completely sequenced the sixteen chromosomes of fourteen diploid cells obtained by RTG from a diploid hybrid yeast in which the homologous chromosomes differ by 63,901 markers of nucleotide polymorphism (SNP) (meaning a marker every 187 bp on the average). They were thus able to determine the number and nature (crossover or gene conversion) of the recombination events that occurred in each of the cells during this process.

They observed, entirely unexpectedly, that the cells issuing from RTG were highly recombinant (3 to 51 recombination events per cell) and were characterized by a very high genetic diversity of homologous chromosomes, with none of the cells having the same recombination profile. In addition, the inventors demonstrated that the cells issuing from RTG showed recombinations associated with loss of heterozygosity of variable lengths involving one or more SNPs. The physical size of the loss of heterozygosity ranged from 2 bp to 700 kb. With this general view of recombination events at the genome scale, the inventors demonstrated that, contrary to what had been previously described, the mechanisms for repairing double-strand breaks during the RTG process did not limit loss of heterozygosity but instead generated a massive diversification of the genetic information from the genome of the parental hybrid cell.

Surprisingly, it thus appeared that the RTG process could be used to generate high genetic diversity. This process is therefore of particular interest for the improvement or modification of hybrid yeasts, particularly sterile hybrid yeasts for which it is impossible to obtain recombinant genotypes from spores.

The invention therefore relates to a method for improving a yeast strain of industrial interest, comprising:

a) transferring the yeast from a rich medium to a sporulation medium, preferably having no source of fermentable carbon or nitrogen;

b) incubating yeasts in the sporulation medium for a length of time sufficient to induce Spo11-dependent double-strand breaks;

c) placing the yeasts in contact with a source of carbon and nitrogen before the reductional chromosome segregation of the first meiotic division in order to obtain recombinant yeasts;

d) collecting the recombinant yeasts; and e) screening or selection of the recombinant yeasts in order to identify those having the desired improvement.

Preferably, the yeast strain of industrial interest has a ploidy level greater than or equal to 2.

The present invention also relates to the use of the yeast RTG process to improve a yeast strain of industrial interest, said RTG process being induced by transferring the yeast from a rich medium to a sporulation medium, preferably having no source of fermentable carbon or nitrogen, incubating the yeasts in the sporulation medium for a length of time sufficient to induce Spo11-dependent double-strand breaks, and placing the yeasts in contact with a source of carbon and nitrogen before the reductional chromosome segregation of the first meiotic division. Preferably, the yeast strain of industrial interest has a ploidy level greater than or equal to 2.

The RTG process involves the yeast initiating a meiotic cycle and double-strand breaks before resuming a mode of mitotic growth. Initiation of the meiotic cycle depends on several signals: the presence of two mating alleles MATa and MATα, the absence of a source of nitrogen and fermentable carbon.

As used herein, the term "rich medium" refers to a culture medium comprising a fermentable carbon source and a nitrogen source and all the nutrients necessary for yeasts to multiply by mitotic division. This medium can readily be selected by a person skilled in the art and may, for example, be chosen from the group consisting of YPD medium (1% yeast extract, 2% Bacto Peptone, and 2% glucose), YPG medium (1% yeast extract, 2% Bacto Peptone, and 3% glycerol) (Treco and Lundblad, 2001), and a synthetic complete medium (or SC medium).

As used herein, the term "sporulation medium" refers to any medium inducing yeast cells to enter the meiotic prophase without vegetative growth, in particular a culture medium containing no fermentable carbon source or nitrogen source but containing a carbon source that can be metabolized by respiration such as acetate. This medium can be readily selected by the skilled person and may, for example, be chosen from the group consisting of 1% KAc medium (Wu and Lichten, 1994), SPM medium (Kassir and Simchen 1991), and the sporulation media described in Sherman (1991).

According to a preferred embodiment, before being incubated in the sporulation medium, the cells are cultured for a few rounds of division in a pre-sporulation medium so as to obtain effective and synchronous sporulation. The pre-sporulation medium can be readily selected by a person skilled in the art. This medium may be SPS medium for example (Wu and Lichten, 1994).

The choice of media (rich medium, pre-sporulation medium, sporulation medium) depends on the physiological and genetic characteristics of the yeast strain to be improved, particularly if this strain is auxotrophic for one or more compounds.

The reversibility of the meiotic prophase is transient. Indeed, if the cells are re-incubated in rich medium before the formation of Spo11-dependent double-strand breaks, they quickly resume their mitotic division with no modification of the genome. Conversely, if the cells are cultured in rich medium after a starting phase occurring just before the reductional chromosome segregation during the first meiotic division (MI), sporulation proceeds normally and generates recombinant spores. Thus the RTG process, creating recombinant genotypes, can occur within a window of time located between the formation of Spo11-dependent double-strand breaks and the starting phase prior to the reductional chromosome segregation in MI.

The length of the incubation in sporulation medium can vary with the yeast strains. For some strains responding more slowly to nutrient deficiency signals, the incubation in this medium can be increased.

The length of the incubation in sporulation medium may be determined by the skilled person for each strain of interest by determining (i) the period of formation of Spo11-dependent double-strand breaks, (ii) the period of reductional chromosome segregation, and (iii) the starting phase before reductional chromosome segregation. Alternatively, the incubation period in sporulation medium may be determined by the skilled person for each strain of interest by determining only the starting phase. Adding a source of carbon and nitrogen may, for example, be envisaged 1, 2, 3, or 4 hours, preferably 1 or 2 hours, before the starting phase.

The formation of Spo11-dependent double-strand breaks can be followed by conventional molecular biology techniques such as Southern blotting. Similarly, it is possible to observe the reductional chromosome segregation by simply marking the DNA, for example by DAPI staining. The starting phase, prior to which the cells must be placed in the presence of a source of carbon and nitrogen, is just before the reductional chromosome segregation. This phase can be determined by conducting RTG experiments where the cells are placed in the presence of a source of carbon and nitrogen at different incubation times. It is thus possible to define the window of time during which the percentage of cells resuming mitotic division (which is evidenced by the birth of a bud cell) is highest (and therefore during which the percentage of cells continuing the sporulation process is lowest). For example, for the *Saccharomyces cerevisiae* yeasts of S288C or SK1 genetic background as used in the experimental part, this window of time is 5 to 7 hours after transferring the cells to the sporulation medium.

For the exposure to a carbon and nitrogen source again, the yeasts can be transferred to a rich medium as described above. Alternatively, a carbon source and a nitrogen source can be added directly to the sporulation medium.

The carbon source can be any fermentable carbon source and may, for example, be selected from the group consisting of glucose, galactose, glycerol, sucrose, fructose, and maltose. The nitrogen source may, for example, be selected from the group consisting of inorganic nitrogen such as ammonium sulfate, ammonium phosphate, sodium nitrate, ammonium nitrate, or potassium nitrate, and organic nitrogen for example in the form of amino acids (glutamate, glutamine) or yeast extracts (Albers et al., 1996).

The yeasts placed in contact with a source of fermentable carbon and nitrogen resume mitotic division after an adjustment period during which the double-strand breaks are repaired. The numerous recombination events observed by the inventors take place during this period as these breaks are repaired. The duration of the adjustment period can vary depending on the species and is easily adjusted by the skilled person. In general, it may take from 1 to 3 hours, preferably about 1.5 hours.

After this adjustment period, the recombinant yeasts may be retrieved (step d) of the method) for screening or selection. Optionally, prior to screening or selection, they may be preserved in the form of recombinant yeast libraries.

The yeast strain of industrial interest may be haploid (n chromosomes), diploid (2n chromosomes), or polyploid (2n, 3n, 4n, or more chromosomes). The yeast strain of industrial interest may also be aneuploid, meaning its ploidy level is not an exact multiple of the haploid number. In this case, the yeast may comprise, for example, n+x, 2n+x, or 3n+x chromosomes, where x is the number of additional chromosomes beyond the exact multiple of the haploid number. The yeast may, for example, have one or more disomies, meaning two copies of one or more chromosomes (for example n+1, n+2, or n+3 chromosomes), or one or more trisomies, meaning three copies of one or more chromosomes (for example n+2, 2n+1, or 2n+2 chromosomes).

According to one particular embodiment, the yeast strain of industrial interest comprises at least one disomy.

Preferably, the yeast strain of industrial interest has a ploidy level greater than or equal to 2. In particular, it may be diploid (2n), aneuploid (for example 2n+x or 3n+x), or polyploid (for example 3n, 4n, or 5n), preferably diploid.

To be subjected to the RTG process, the yeast strain of interest is capable of entering sporulation and progressing to the stage of forming double-strand breaks. However, it may be deficient for later stages and unable to form mature and/or viable spores. Entering sporulation is dependent on a mating signal composed of two alleles a and a. In the case where the yeast is haploid or aneuploid and comprises only one of these alleles, it is possible to induce mutations leading to expression of the two mating types (for example mutations in the sir genes that regulate expression of HMR and HML mating loci) or to introduce into the genome a mating gene carrying the missing allele. Such changes have been described for example in *Saccharomyces cerevisiae* to induce the entry of haploid strains into meiosis (De Massy et al., 1994).

According to a preferred embodiment, the yeast strain of industrial interest is a hybrid yeast, preferably a diploid hybrid yeast. In particular, the yeast strain of industrial interest can be obtained by crossing a strain of interest with another genetically distinct strain having a characteristic of interest. The hybrid cell so obtained is then transferred to the sporulation medium (step a) of the method). The method of the invention may thus further comprise, prior to step a), the steps of (i) selecting a yeast strain genetically distinct from a yeast strain of industrial interest and having a characteristic of interest intended to improve said strain, and (ii) crossing the strain of interest and the genetically distinct strain in order to obtain a hybrid strain. The genetic traits of the two parent strains are then recombined using the method according to the invention.

The term "hybrid yeast" or "hybrid strain" as used herein refers to a yeast obtained by crossing two genetically distinct strains, meaning two strains having a difference in their genotype or in at least one genetic trait. Preferably, the parent strains differ in at least one phenotypic characteristic, such as growth rate, thermotolerance, cryotolerance, pH sensitivity, fermentability and fermentation rate, resistance to ethanol or to any other compound present in the fermentation medium or excreted from the cell culture, cell morphology, flocculation, sensitivity to a particular molecule, efficiency of sporulation, aromatic profiles, nutritional requirements, resistance to drying, or fermentation of a particular sugar. The hybrid yeasts may be diploid, aneuploid, polyploid, and in particular allopolyploid, meaning comprising several sets of chromosomes from different species. The hybrid yeast is preferably diploid. The nature of the hybrid may be intra- or interspecies, preferably interspecies. Interspecies hybrids are usually sterile. Hybrid yeasts can be obtained by methods well known to those skilled in the art, in particular by fusing two spores or two protoplasts (somatic hybridization).

Yeasts from intra- or interspecies hybridizations are commonly used in industry. Hybridization can be used to create new yeast strains offering a combination of characteristics from the parent strains. For the wine industry, for example, it may be of interest to cross a strain having good resistance to ethanol with a strain resistant to high temperatures. The hybrids combining the characteristics of interest from the parent strains are then selected.

One of the major disadvantages to the use of hybrid strains lies in the fact that these strains are frequently sterile. The sterility of a strain may be due to its inability to produce mature spores or to the non-viability of the spores. For example, the diploid hybrid yeasts obtained by fusing *Saccharomyces cerevisiae* and *Saccharomyces paradoxus* and used in the production of red wine are able to multiply by mitotic growth but are unable to produce viable haploid gametes (Greig, 2007). These sterile hybrid strains therefore cannot be further modified by crossing descendants or by fusing with other strains of interest.

However, these strains can be recombined using the method of the invention. Thus, in one preferred embodiment, the yeast strain of industrial interest is a sterile hybrid strain, and in particular a sterile diploid hybrid strain. Indeed, the inventors demonstrated that the RTG process allowed obtaining highly recombinant strains without it being necessary to complete the sporulation process. The method of the invention therefore allows obtaining highly recombinant cells from sterile hybrids and thus improving a hybrid strain without the use of recombinant DNA techniques.

The term "sterile yeast" as used herein refers to a yeast incapable of or having a reduced capacity for producing mature spores, and/or a yeast having spores that are non-viable or of reduced viability. The sterile yeast is, however, capable of entering sporulation and progressing to the stage of forming double-strand breaks. Sterile yeast may have a capacity to produce mature spores that is reduced by 50, 60, 70, 80, 90, 95, or 99% compared to a reference strain of the same species, or in the case of a hybrid yeast, compared to one of the parent strains. The sterile yeast may also produce spores of reduced viability. In particular, among the spores produced by this yeast, at least 25, 50, or 75% of the spores may be non-viable. Preferably, the sterile strain is unable to produce mature spores or does not produce viable spores.

The yeast strain of industrial interest may be intended for or used in any industrial process, particularly in food industry processes such as wine making, brewing, distilling, or bread making, in biofuel production, in the production of useful molecules, or in the degradation of cellulose.

The strain of industrial interest may be any yeast strain that, when put back in the presence of a source of carbon and nitrogen, is able to resume mitotic division after induction of double-strand breaks in meiotic prophase.

According to a preferred embodiment, the yeast strain of industrial interest is a non-genetically modified organism. As used herein, the term "non-genetically modified organism" refers to yeasts whose genetic material has not been altered by genetic engineering, in particular by transgenesis.

Preferably, the recombinant yeasts produced by the method of the invention are not considered to be genetically modified organisms (GMOs).

According to one particular embodiment, the yeast strain of industrial interest belongs to the genus *Saccharomyces sensu stricto* or is a hybrid obtained from a strain belonging to the genus *Saccharomyces sensu stricto*. Preferably, the yeast strain of industrial interest belongs to a species chosen from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus,* and *Saccharomyces pastorianus* (also known as *Saccharomyces carlsbergensis*) or is a hybrid obtained from a strain of one of these species. Even more preferably, the yeast strain of industrial interest is of the species *Saccharomyces cerevisiae* or a hybrid obtained from a strain of the species *Saccharomyces cerevisiae*, such as a *S. cerevisiae/S. paradoxus* hybrid or a *S. cerevisiae/S. uvarum* hybrid (Ranieri et al., 1999).

According to one embodiment, the recombinant cells obtained after the RTG process (step d) of the method according to the invention) are highly recombinant and have several recombination events per cell, preferably more than 2, 3, 5, 10, 15, 20, 25, 30, 35, 40, 45, or 50 recombination events per cell. Each event may be a crossover, a gene conversion, or a gene conversion associated with a crossover depending on the mechanism involved in repairing the double-strand break. As used herein, the term "recombination event" refers to a recombination junction observed in the genotype of a cell issuing from the RTG (i) between a monoallelic region, preferably of at least 20 kb, and a biallelic region, or (ii) between two monoallelic regions of different alleles, preferably one of these regions having a size of at least 20 kb.

According to one particular embodiment, the recombination events induce a decrease in the level of heterozygosity. This means that the recombination events result in loss of heterozygosity. The creation of homozygous regions is of particular interest in strain improvement processes since it allows the expression of potentially interesting recessive traits. The decrease in the level of heterozygosity can be evaluated, for example, by tracking markers of genetic polymorphism, in particular nucleotide polymorphism.

Another advantage of the method of the invention is that the recombinant cells can have a ploidy level greater than or equal to 2, preferably equal to 2. Because of this, quantitative traits expressing the heterozygous state (heterosis phenomenon) can easily be analyzed and the recombinant cells can in turn be directly used according to the method of the invention for other recombinations.

In one embodiment, the recombinant yeasts are again transferred to a sporulation medium, preferably without a source of fermentable carbon or nitrogen, to induce entry of the yeasts into meiotic prophase, are incubated in the sporulation medium for a length of time sufficient to induce Spo11-dependent double-strand breaks, and are placed in contact with a source of carbon and nitrogen before the reductional chromosome segregation of the first meiotic division before being collected. Screening or selection of the recombinant yeasts can take place at the end of each cycle or after several cycles. When the screening or selection of the recombinant yeasts takes place at the end of each cycle, only the selected yeasts can again undergo the improvement process. Steps a) to d) or a) to e) of the method of the invention may thus be repeated one or more times. In particular, steps a) to d) or a) to e) of the method of the invention may be repeated at least 1, 2, 3, 4, or 5 times. Preferably, steps a) to d) of the method of the invention may be repeated at least 1, 2, 3, 4, or 5 times, prior to screening or selection of the recombinant yeasts having the desired improvement.

Optionally, the recombinant yeasts collected in step d) or selected in step e) can be induced for sporulation to obtain haploid spores. Spores of a tetrad obtained from a recombinant cell may be sequenced to determine the haplotype of the chromosomes of said recombinant cell. Alternatively, the recombinant yeasts collected in step d) or selected in step e) may be left to bud to obtain "mother/daughter" cell pairs. These mother/daughter cells obtained from a recombinant cell can be sequenced to determine the haplotype of the chromosomes of said recombinant cell.

The method of the invention may further comprise other steps to increase or to target recombination events in the yeasts during the RTG process. According to one embodiment, when the yeasts are in the sporulation medium (step a) of the method), they are exposed to one or more chemical mutagenic agents such as methyl methanesulfonate (MMS) or physical ones such as ultraviolet or ionizing radiation. This exposure allows dual genetic diversification through recombination of polymorphic markers and random mutagenesis.

According to another embodiment, a nucleic acid construct as described in European Patent No. 1523564 is introduced into the yeast to be improved, before it is transferred into the sporulation medium. This nucleic acid encodes a fusion protein, controlled by a meiosis-specific or non-meiosis-specific promoter, preferably specific, comprising a DNA-binding domain (for example Gal4BD) operably linked to a Spo11 protein, and allows increasing the frequency of double-strand breaks in certain chromosomal regions in meiotic prophase or modifies the distribution of such breaks throughout the genome. Alternatively, the fusion protein comprises, controlled by a meiosis-specific promoter, a DNA-binding domain operably linked to a partner protein of Spo11 involved in the formation of double-strand breaks and capable of recruiting Spo11. The partner protein of Spo11 may be chosen from those described by Keeney (2001), Smith and Nicolas (1998), and Acquaviva et al. (2012). In particular, it may be chosen from the group consisting of ME14, MER2/REC107, REC102, REC104, REC114, REC103/SK18, MRE2/NAM8, MRE11, RAD50, XRS2/NBS1, HOP1, RED1, MER1, MEK1, SET1, and SPP1.

The screening or selection of the recombinant yeasts providing the desired improvement can be done by any method known to those skilled in the art, and depends upon the characteristic desired. Because of the wide variety of industrial applications for yeast, in particular yeasts of the species Saccharomyces cerevisiae, many characteristics can be improved using the method of the invention. For example, these characteristics may be the growth rate, particularly under specific conditions, resistance to high temperatures (thermotolerance) or, conversely, to low temperatures (cryotolerance), pH sensitivity, fermentability and fermentation rate, resistance to ethanol or to any other compound present in the fermentation medium or excreted from the cell culture, cell morphology, flocculation, sensitivity to a particular molecule, efficiency of sporulation, aromatic profiles, nutritional requirements, resistance to drying, or fermentation of a particular sugar.

The present invention also relates to a recombinant yeast obtained according to the improvement method of the invention, or to a yeast derived from it.

The inventors have demonstrated, by complete sequencing of the genome of cells issuing from the RTG process, that it would generate a wide genetic diversity and that none of the cells resulting from this process have the same recombination profile.

Thus, according to another aspect, the present invention relates to the use of the yeast RTG process to generate a recombinant yeast library from one yeast, said RTG process being induced by transferring said yeast from a rich medium to a sporulation medium, preferably having no source of fermentable carbon or nitrogen, incubating in the sporulation medium for a length of time sufficient to induce Spo1-dependent double-strand breaks, and placing the yeast in contact with a source of carbon and nitrogen before the reductional chromosome segregation of the first meiotic division.

Preferably, the yeast has a ploidy level greater than or equal to 2, and more preferably is diploid. Preferably, said yeast is a hybrid strain, in particular a sterile hybrid strain.

It also relates to a method for generating a recombinant yeast library from a yeast, preferably a yeast having a ploidy level greater than or equal to 2, comprising:

a) transferring the yeast from a rich medium to a sporulation medium, preferably having no source of fermentable carbon or nitrogen;

b) incubating the yeasts in the sporulation medium for a length of time sufficient to induce Spo11-dependent double-strand breaks;

c) placing the yeasts in contact with a source of carbon and nitrogen before the reductional chromosome segregation of the first meiotic division in order to obtain recombinant yeasts;

d) collecting the recombinant yeasts to form a recombinant yeast library.

The embodiments described above for the improvement process according to the invention also apply to this aspect.

According to a preferred embodiment, the diploid recombinant yeasts have several recombination events per cell, preferably more than 2, 3, 5, 10, 15, 20, 25, 30, 35, 40, 45, or 50 recombination events per cell.

According to one embodiment, the method further comprises, prior to step a), the step of obtaining the yeast preferably having a ploidy level greater than or equal to 2 by crossing two yeasts of interest.

Preferably, the yeast having a ploidy level greater than or equal to 2 is diploid. Preferably, said yeast is a hybrid strain, in particular a sterile hybrid strain. According to a preferred embodiment, the yeast is a strain of industrial interest, in particular a diploid strain of industrial interest. More preferably, the yeast is of the genus *Saccharomyces sensu stricto*, more particularly the species *S. cerevisiae*, or is a hybrid obtained from a strain of the genus *Saccharomyces sensu stricto*, more particularly the species *S. cerevisiae*.

The yeast library so generated may in particular be used to select yeast strains having particular characteristics or to locate a genetic trait of interest, particularly a quantitative trait of interest (QTL), by comparing the genotypes and phenotypes of the recombinant yeasts.

The present invention also relates to a recombinant yeast library obtained by the method for generating a yeast library according to the invention.

The present invention also relates to a method for identifying or locating the genetic information encoding a characteristic of interest in a yeast, preferably a yeast having a ploidy level greater than or equal to 2, comprising:

a) transferring the yeast from a rich medium to a sporulation medium, preferably having no source of fermentable carbon or nitrogen;

b) incubating the yeasts in the sporulation medium for a length of time sufficient to induce Spo11-dependent double-strand breaks;

c) placing the yeasts in contact with a source of carbon and nitrogen before the reductional chromosome segregation of the first meiotic division in order to obtain recombinant yeasts;

d) collecting the recombinant yeasts; and e) analyzing the genotypes and phenotypes of the recombinant yeasts to identify or locate the genetic information encoding the characteristic of interest.

It also relates to the use of the yeast RTG process to identify or locate genetic information encoding a characteristic of interest in a yeast, preferably a yeast having a ploidy level greater than or equal to 2, said RTG process being induced by transferring the yeast from a rich medium to a sporulation medium, preferably having no source of fermentable carbon or nitrogen, incubating the yeasts in the sporulation medium for a period sufficient to induce Spo11-dependent double-strand breaks, and placing the yeasts in contact with a source of carbon and nitrogen before the reductional chromosome segregation of the first meiotic division.

Preferably, the characteristic of interest is a quantitative trait of interest (QTL).

The embodiments described above for the improvement process according to the invention also apply to this aspect.

The inventors also showed that of the 63,901 markers of single nucleotide polymorphism (SNP) analyzed, on the average 27% of them showed loss of heterozygosity in the cells issuing from RTG. This observation is all the more surprising in that it contradicts the teachings of the prior art which indicated that the mechanisms for repairing the double-strand breaks introduced during RTG seemed to minimize the resolution of breaks by crossing-over phenomena in order to preserve the integrity of the genome and limit the loss of heterozygosity.

Thus, according to yet another aspect, the present invention relates to the use of the RTG process to reduce the level of heterozygosity of a yeast, preferably a yeast having a ploidy level greater than or equal to 2, in particular a diploid hybrid yeast, said RTG process being induced by transferring the yeast from a rich medium to a sporulation medium, preferably having no source of fermentable carbon or nitrogen, incubating the yeasts in the sporulation medium for a length of time sufficient to induce Spo1-dependent double-strand breaks, and placing the yeast in contact with a source of carbon and nitrogen before the reductional chromosome segregation of the first meiotic division.

It also relates to a method for decreasing the level of heterozygosity of a yeast, preferably a yeast having a ploidy level greater than or equal to 2, in particular a diploid hybrid yeast, comprising:

a) transferring the yeast from a rich medium to a sporulation medium, preferably having no source of fermentable carbon or nitrogen;

b) incubating the yeasts in the sporulation medium for a length of time sufficient to induce Spo11-dependent double-strand breaks;

c) placing the yeast in contact with a source of carbon and nitrogen before the reductional chromosome segregation of the first meiotic division in order to obtain recombinant yeasts; and d) collecting the recombinant yeasts, said recombinant yeasts having a lower level of heterozygosity than that of the yeast of step a).

The embodiments described above for the improvement process of the invention also apply to this aspect.

Preferably, the yeast having a ploidy level greater than or equal to 2 is diploid. Preferably, said yeast is a hybrid strain, in particular a sterile hybrid strain, preferably of industrial interest. More preferably, the yeast is of the genus *Saccharomyces sensu stricto*, more particularly of the species *S. cerevisiae*, or is a hybrid obtained from a strain of the genus *Saccharomyces sensu stricto*, more particularly of the species *S. cerevisiae*.

The following examples are presented for illustrative and non-limiting purposes.

Examples

Materials and Methods:
Yeast Strains

The information concerning the strains used, their origin, and their genotype is indicated in Table 1 below.

TABLE 1

Information concerning the strains used

| Name | Origin | Genetic background | Genotype |
|---|---|---|---|
| ORT3805 | A. Nicolas | S288C | MATa, his1 |
| ORT3806 | A. Nicolas | S288C | MATα, his1 |
| Y00981 | (a) | S288C | MATa, his3Δ1, leu2Δ0, met15Δ0, ura3Δ0, arg4Δ::KanMX |
| ORT7204 | Y00981 | S288C | MATa, his3Δ1, leu2Δ0, met15Δ0, ura3Δ0, arg4Δ::URA3 |
| ORT7219 | (b) | S288C | MATα, ho, lys2Δ0, ura3Δ0, leu2Δ0, his3Δ200, met15Δ0, trp1Δ63 |
| ORT7205 | ORT7219 | S288C | MATα, ho, lys2Δ0, ura3Δ0, arg4Δ::URA3, leu2Δ0, his3Δ200, met15Δ0, trp1Δ63 |
| ORT7235 | ORT7205 | S288C | MATα, ho, lys2Δ0, ura3Δ0, arg4-Bgl, leu2Δ0, his3Δ200, met15Δ0, trp1Δ63 |
| ORT7221 | (c) | SK1 | MATa, ho, lys2, ura3(PstI-SmaI)::hisG, leu2::hisG, his4B::LEU2, trp1::hisG |
| ORT7217 | ORT7221 | SK1 | MATa, ho, lys2, ura3(PstI-SmaI)::hisG, arg4::URA3, leu2::hisG, his4B::LEU2, trp1::hisG |
| ORT7236 | ORT7217 | SK1 | MATa, ho, lys2, ura3(PstI-SmaI)::hisG, arg4-RV, leu2::hisG, his4B::LEU2, trp1::hisG |
| AND1702 | ORT7235 × ORT7236 | Hybrid S288C-SK1 | MATa/MATα, ho/ho, arg4-Bgl/arg4-RV, lys2Δ0/lys2, ura3(PstI-SmaI)::hisG/ura3Δ0, leu2Δ0/leu2::hisG, his3Δ200/HIS3, met15Δ0/MET15, trp1Δ63/trp1::hisG, his4B::LEU2/HIS4 |
| AND1708 | AND1702 | Hybrid S288C-SK1 | MATa/MATα, ho/ho, ARG4/arg4-Bgl, lys2Δ0/lys2Δ0, ura3Δ0/ura3(PstI-SmaI)::hisG, trp1Δ63/trp1::hisG;, leu2Δ0/leu2::hisG his4B::LEU2/his4B::LEU2, his3Δ200/his3Δ200, MET15/met15Δ0 |
| AND1709 | AND1702 | Hybrid S288C-SK1 | MATa/MATα, ho/ho, lys2Δ0/lys2Δ0, ura3Δ0/ura3(recombinantΔ0-(PstI-SmaI)::hisG), trp1Δ63/trp1::hisG, leu2Δ0/leu2::hisG, HIS4/his4B::LEU2, his3Δ200/his3Δ200 |
| AND1710 | AND1702 | Hybrid S288C-SK1 | MATa/MATα, ho/ho, lys2Δ0/lys2Δ0, ura3Δ0/ura3(recombinant Δ0-(PstI-SmaI)::hisG), trp1Δ63/trp1::hisG, leu2Δ0/leu2::hisG, HIS4/his4B::LEU2, his3Δ200/his3Δ200, |
| AND1711 | AND1702 | Hybrid S288C-SK1 | MATa/MATα, ho/ho, ARG4/arg4-RV, lys2Δ0/lys2Δ0, ura3Δ0/ura3(PstI-SmaI)::hisG, trp1Δ63/trp1::hisG, leu2Δ0/leu2::hisG, HIS4/his4B::LEU2, his3Δ200/his3Δ200 |
| AND1712 | AND1702 | Hybrid S288C-SK1 | MATa/MATα, ho/ho, ARG4/arg4-RV, lys2Δ0/lys2, ura3Δ0/ura3(PstI-SmaI)::hisG, trp1Δ63/trp1::hisG, leu2Δ0/leu2::hisG, HIS4/his4B::LEU2, his3Δ200/his3Δ200, MET15/met15Δ0 |
| AND1720 | AN1702 | Hybrid S288C-SK1 | MATa/MATα, ho/ho, ARG4/arg4-Bgl, lys2Δ0/lys2, ura3Δ0/ura3(PstI-SmaI)::hisG, trp1Δ63/trp1::hisG, leu2Δ0/leu2::hisG, HIS4/his4B::LEU2, his3Δ200/HIS3, met15Δ0/met15Δ0 |
| AND1733(M) | AND1702 | Hybrid S288C-SK1 | MATa/MATα, ho/ho, ARG4/arg4-Bgl, lys2Δ0/lys2; ura3Δ0/ura3(PstI-SmaI)::hisG, trp1Δ63/trp1::hisG, leu2::hisG/leu2::hisG, his4B::LEU2/his4B::LEU2, MET15/met15Δ0 |

TABLE 1-continued

Information concerning the strains used

| Name | Origin | Genetic background | Genotype |
|---|---|---|---|
| AND1734(D) | AND1702 | Hybrid S288C-SK1 | MATa/MATα, ho/ho, arg4-Bgl/arg4-RV, lys2Δ0/lys2, ura3Δ0/ura3(PstI-SmaI)::hisG, trp1Δ63/trp1::hisG, leu2Δ0/leu2Δ0, MET15/met15Δ0 |
| AND1735(M) | AND1702 | Hybrid S288C-SK1 | MATa/MATα, ho/ho, arg4-Bgl/arg4-RV, lys2Δ0/lys2, ura3Δ0/ura3(PstI-SmaI)::hisG, trp1Δ63/trp1::hisG, leu2Δ0/leu2::hisG; his3Δ200/his3Δ200, his4B::LEU2/HIS4, MET15/met15Δ0 |
| AND1736(D) | AND1702 | Hybrid S288C-SK1 | MATa/MATα, ho/ho, arg4-Bgl/arg4-RV, lys2Δ0/lys2, ura3Δ0/ura3(PstI-SmaI)::hisG, trp1Δ63/trp1::hisG, leu2Δ0/leu2::hisG, his4B::LEU2/HIS4, MET15/met15Δ0 |
| AND1737(M) | AND1702 | Hybrid S288C-SK1 | MATa/MATα, ho/ho, arg4-Bgl/arg4-RV, lys2Δ0/lys2, ura3Δ0/ura3(PstI-SmaI)::hisG, trp1Δ63/trp1::hisG, leu2Δ0/leu2Δ0, HIS3/his3Δ200, MET15/met15Δ0 |
| AND1738(D) | AND1702 | Hybrid S288C-SK1 | MATa/MATα, ho/ho, arg4-Bgl/arg4-RV, lys2Δ0/lys2, ura3Δ0/ura3(PstI-SmaI)::hisG, trp1Δ63/trp1::hisG, leu2::hisG/leu2::hisG, his3Δ200/HIS3, his4B::LEU2/his4B::LEU2, MET15/met15Δ0 |
| AND1739(M) | AND1702 | Hybrid S288C-SK1 | MATa/MATα, ho/ho, arg4-Bgl/arg4-RV, lys2Δ0/lys2, ura3Δ0/ura3(PstI-SmaI)::hisG, trp1Δ63/trp1::hisG, leu2Δ0/leu2::hisG; HIS4/his4B::LEU2, MET15/met15Δ0 |
| AND1740(F) | AND1702 | Hybrid S288C-SK1 | MATa/MATα, ho/ho, arg4-Bgl/arg4-RV, lys2Δ0/lys2, ura3Δ0/ura3(PstI-SmaI)::hisG, trp1Δ63/trp1::hisG, leu2Δ0/leu2::hisG, his3Δ200/his3Δ200, HIS4/his4B::LEU2, MET15/met15Δ0 |
| AND1710-1A | AND1710 | Hybrid S288C-SK1 | MATα, ho, ARG4, lys2Δ0, ura3Δ0, trp1::hisG, leu2::hisG, his3Δ200, |
| AND1710-1B | AND1710 | Hybrid S288C-SK1 | MATa, ho, ARG4, lys2Δ0, ura3(recombinant Δ0-(PstI-SmaI)::hisG), trp1Δ63, leu2Δ0, his3Δ200, his4B::LEU2 |
| AND1710-1C | AND1710 | Hybrid S288C-SK1 | MATa, ho, ARG4, lys2Δ0, ura3Δ0, trp1::hisG, leu2::hisG, his3Δ200, his4B::LEU2 |
| AND1710-1D | AND1710 | Hybrid S288C-SK1 | MATα, ho, ARG4, lys2Δ0, ura3(recombinant Δ0-(PstI-SmaI)::hisG), trp1Δ63, leu2Δ0, his3Δ200 |
| AND2711 | AND1735 | Hybrid S288C-SK1 | MATα/MATa, ho/ho, arg4-Bgl/arg4-RV, lys2/lys2, ura3Δ0/ura3(PstI-SmaI)::hisG, leu2Δ0/leu2::hisG, trp1Δ63/trp1::hisG, his3Δ200/his3Δ200, HIS4/his4B::LEU2 |
| AND2907 | AND2711 | Hybrid S288C-SK1 | MATa/MATa, ho/ho, arg4-Bgl/arg4-RV, lys2/lys2, ura3Δ0/ura3(PstI-SmaI)::hisG, leu2Δ0/leu2::hisG, trp1Δ63/trp1::hisG, his3Δ200/his3Δ200, HIS4/his4B::LEU2 |
| ORT7469 | ORT7235 | S288C- | MATα, ho, lys2Δ0, ura3Δ0, arg4-Bgl, leu2Δ0, his3Δ200, met15Δ0, trp1Δ63, ndt80::KanMX |
| ORT7477 | ORT7237 | SK1 | MATa, ho, lys2, ura3(PstI-SmaI)::hisG, arg4-RV, leu2::hisG, his4B::LEU2,, trp1::hisG, ndt80::KanMX |
| AND2248 | ORT7469 × ORT7477 | Hybrid S288C-SK1 | MATa/MATα, ho/ho, lys2/lys2Δ0, ura3(PstI-SmaI)::hisG/ura3Δ0, arg4-RV/arg4-Bgl, leu2::hisG/leu2Δ0, HIS3/his3Δ200, his4B::LEU2/HIS4, MET15/met15Δ0, trp1::hisG/trp1Δ63, ndt80::KanMX/ndt80::KanMX |
| AND2642 | AND2248 | Hybrid S288C-SK1 | MATα/MATa, ho/ho, arg4-Bgl/arg4-RV, lys2/lys2, ura3Δ0/ura3(PstI-SmaI)::hisG, leu2Δ0/leu2::hisG, his3Δ200/HIS3, met15Δ0/met15Δ0, trp1Δ63/trp1::hisG, HIS4/his4B::LEU2, ndt80Δ::kanMX/ndt80::kanMX |
| AND2652 | AND2248 | Hybrid S288C-SK1 | MATα/MATa; ho/ho; arg4-Bgl/arg4-RV; lys2Δ0/lys2; ura3Δ0/ura3(PstI-SmaI)::hisG; leu2Δ0/leu2::hisG; his3Δ200/HIS3; met15Δ0/MET15; trp1Δ63/trp1::hisG; his4B::LEU2/his4B::LEU2; ndt80Δ::kanMX/ndt80Δ::kanMX |
| AND2658 | AND2248 | Hybrid S288C-SK1 | MATα/MATa; ho/ho; arg4-Bgl, RV/arg4-RV; lys2Δ0/lys2; ura3Δ0/ura3(PstI-SmaI)::hisG; leu2Δ0/leu2::hisG; his3Δ200/his3Δ200; met15Δ0/MET15; trp1Δ63/trp1::hisG; HIS4/his4B::LEU2; ndt80Δ::kanMX/ndt80Δ::kanMX |

(a) EUROSCARF (http://web.uni-frankfurt.de/fb15/mikro/euroscarf/data/YHR018c.html)
(b) Ben-Ari et al., 2006, strain FY1338
(c) Kane and Roth, 1974, strain derived from SK-1
(M) mother cell
(D) daughter cell These are yeast strains of the genus *Saccharomyces cerevisiae*, the genetic background being S288C (Mortimer and Johnston, 1986) or SK1 (Kane and Roth, 1974). The strains ORT7235 and ORT7236, carriers of arg4-Bgl and arg4-RV mutations respectively, were obtained in two transformation steps.

Beforehand, strain Y00981 from the EUROSCARF deletion collection (http://web.uni-frankfurt.de/fb15/mikro/euroscarf/data/YHR018c.html), in which the ARG4 gene is replaced with KanMX, was transformed by the electroporation method (Becker and Guarente, 1991) with plasmid M4758 (Voth et al., 2003) in order to replace KanMX with the URA3 gene at the ARG4 locus. RL1 and RL2 primers (described in Table 2) were used to amplify the fragment arg4Δ::URA3.

TABLE 2

Description of primers used to amplify the ARG4 locus

| Name | Description | Sequence | Coordinates |
|---|---|---|---|
| RL1 | fwd-arg4-220 | 3'-TACTCATTGGCAGAATC CCG-5'(SEQ ID NO: 1) | Chr. VIII: 141604-141623 |
| RL2 | rev-arg4-240 | 3'-CGCTTGAGAGGAAGATT AGC-5'(SEQ ID NO: 2) | Chr. VIII: 139771-139790 |

To obtain the ORT7235 strain, the ORT7219 strain [ARG+ ura−] was transformed by the electroporation method, integrating the PCR product arg4Δ::URA3 at the ARG4 locus. The obtained transformant, ORT7205 [arg− URA+], selected on uracil dropout medium, was then transformed by the electroporation method with the arg4-BgI fragment obtained by digestion of pMY232 plasmid (Rocco et al., 1992) by PstI restriction enzyme. The resulting transformant, ORT7235 [arg− ura−], was selected on 5-FOA medium.

To obtain the ORT7236 strain, the ORT7221 strain [ARG+ ura−] was transformed by the electroporation method, integrating the PCR product arg4Δ::URA3 at the ARG4 locus. The obtained transformant, ORT7217 [arg− URA+], selected on uracil dropout medium, was then transformed by the lithium-acetate method (Schiestl and Gietz, 1989) with the arg4-RV fragment obtained by digestion of pNPS308 plasmid (Rocco et al., 1992) by PstI restriction enzyme. The resulting transformant, ORT7236 [arg− ura−] was selected on 5-FOA medium.

The AND1702 diploid strain was obtained by crossing haploid strains ORT7235 and ORT7236. Both parental strains of the genotypes his3Δ200 and his4::LEU2, respectively, are auxotrophic for histidine but the resulting diploid is prototrophic for histidine by functional complementation and was therefore able to be selected on histidine dropout medium. Thus, the AND1702 strain has a S288C-SK1 hybrid genetic background and is heterozygous for the genetic markers MATa/MATα, arg4-Bgl/arg4-RV, lys2Δ0/lys2, ura3(PstI-SmaI)::hisG/ura3Δ0, leu2Δ0/leu2::hisG, his3Δ200/HIS3, met15Δ0/MET15, trp1Δ63/trp1::hisG, and his4B::LEU2/HIS4, and for all polymorphism markers that differentiate the genome of the two parental strains.

To obtain the AND2248 strain, the ORT7235 and ORT7236 strains were transformed by the electroporation method, integrating the PCR product ndt80::KanMX at the NDT80 locus. The two resulting strains, ORT7469 and ORT7477, were crossed to create the diploid strain AND2248.

Composition of Culture Media Used

YPD growth medium is a rich medium composed of: 1% yeast extract, 2% Bacto Peptone, 2% glucose (2% Bacto Agar if solid media), pH 5.5, H$_2$O adjusted to 1 liter (Treco and Lundblad, 2001). YPD medium containing sodium arsenite (NaASO$_2$) is supplemented to a final concentration of 1.5 mM.

YPG growth medium is a medium for the selection of respiration-capable cells, composed of: 1% yeast extract, 2% Bacto Peptone, 3% glycerol, 2% Bacto Agar, H$_2$O adjusted to 1 liter (Treco and Lundblad, 2001). YPG medium+ geneticin (200 mg/l) allows the selection of strains resistant to geneticin, resulting from expression of the KanMX gene.

X dropout media are complete synthetic media from which a nutrient (X) has been "dropped out", while all others are present (for example, in arginine dropout medium, all nutrients are present except arginine). They enable the selection of strains prototrophic for nutrient X and are composed of: 0.17% yeast nitrogen base without amino acid and without ammonium sulfate, 0.5% ammonium sulfate, 2% glucose, 2% Bacto Agar, supplemented with the nutrients minus one, H$_2$O adjusted to 1 liter. The nutrients are added in the following amounts: 0.002% arginine/histidine/methionine/uracil, 0.003% lysine/tyrosine, 0.004% adenine/tryptophan, 0.005% phenylalanine, 0.006% leucine, 0.01% aspartic acid/glutamic acid, 0.015% valine, 0.02% threonine, and 0.0375% serine. The amino acids not listed can be added at 0.004% (Treco and Lundblad, 2001). The complete synthetic growth medium or SC is equivalent to the dropout medium but with no nutrient omission.

DOBA medium is a minimal medium on which only prototrophic cells can grow. It consists of 0.17% yeast nitrogen base without amino acid and without ammonium sulfate, 0.5% ammonium sulfate, 2% glucose, 2% Bacto Agar, H$_2$O adjusted to 1 liter (Treco and Lundblad, 2001). It allows the selection of diploids resulting from crossing any HIS1 strain with one of the test strains MATa his1 (ORT3805) or MATα his1 (ORT3806) by functional complementation.

5-FOA medium is a medium for selecting ura3− strains, consisting of 2% TRP dropout, 0.17% yeast nitrogen base without amino acid and without ammonium sulfate, 0.5% ammonium sulfate, 0.00204% tryptophan, 0.003% uracil, 0.15% 5-fluoroorotic acid, 2% glucose, 2% Bacto Agar, pH 4.5, H$_2$O adjusted to 1 liter (Treco and Lundblad, 2001).

SPS growth medium is a depleted pre-sporulation medium composed of 0.5% yeast extract, 1% Bacto Peptone, 0.17% yeast nitrogen base without amino acids and without ammonium sulfate, 0.5% ammonium sulfate, 1% potassium acetate, 1.02% potassium biphthalate, pH5.5, H$_2$O adjusted to 1 liter (Wu and Lichten, 1994). 1% KAc medium is a depleted sporulation medium composed of 1% potassium acetate (supplemented or not with 0.001% amino acid depending on the auxotrophies carried by the strains, and with 0.001% PPG2000), H$_2$O adjusted to 1 liter (Wu and Lichten, 1994).

Sporulation Protocol

The diploid strain was streaked on a YPD dish from stock stored at −80° C. After three days of growth at 30° C., cells from a single colony were placed on a dish containing solid YPG medium. After about 6 hours of incubation at 30° C., the cells were suspended in 5 ml liquid YPD and incubated 24 h at 30° C. while stirring (250 rpm). This pre-culture was used to inoculate 50 ml SPS medium at a concentration of $10^5$ cells/ml, which were then incubated about 18 hours at 30° C. until reaching $2\text{-}4.10^7$ cells/ml. The cells were washed in 50 mL 1% KAc medium preheated to 30° C., then centrifuged and resuspended in 100 ml preheated 1% KAc sporulation medium. The cultures were incubated at 30° C. while stirring (250 rpm) for varying times depending on experimental requirements. Samples were collected at different times during sporulation (Wu and Lichten, 1994).

"Return-to-Growth" Protocols

Protocol 1: Isolation by Plating Cells Issuing from RTG.

After incubation for a given time in the sporulation medium, 1 ml culture was collected. The cells were washed in 1 ml H$_2$O (3 min centrifugation at 8000 g), and resuspended in a final volume of 500 µl H$_2$O. At this stage, the cells were plated onto YPD medium (approximately 100 cells/dish, incubation at 30° C.) to grow individual colonies issuing from the RTG process.

Protocol 2: Isolation by Plating Recombinant Cells Issuing from RTG.

As an alternative to Protocol 1, the cells collected during sporulation were deposited on selective arginine dropout medium (approximately 10$^4$ cells/dish) in order to select the recombinant cells carrying an ARG4 allele, allowing growth of the cells in the absence of arginine.

Protocol 3: Isolation by Micromanipulation of RTG Cells.

10 µl of the cell suspension collected during sporulation were deposited in the upper part of a dish of YPD medium. 44 individual non-budding cells were moved by the micromanipulator on the grid of a dissection microscope (Singer MSM System). The dishes were incubated at 30° C. and regularly observed to monitor the appearance of the first daughter cell and to physically separate the mother cell and daughter cell about 4 hours after collection of the sporulation medium. The dishes were incubated at 30° C. in order to obtain pairs of individual "mother/daughter" colonies.

Phenotypic Analysis of Cells Issuing from RTG

Phenotypic Test of Mating Sign.

To test the mating sign of cells issuing from RTG (strains AND1708, AND1709, AND1710, AND1711, AND1712, AND1720, AND1733, AND1734, AND1735, AND1736, AND1737, AND1738, AND1739, AND1740, AND2711, AND2907, AND2642, AND2652, and AND2658) the cells were plated onto YPD solid medium and placed in the presence of MATa his1 (ORT3805) or MATα his1 (ORT3806) haploid test cells. The cell mixture was incubated 24 h at 30° C. then replicated on DOBA medium. The absence of cell growth on this medium reflects the inability of the test cells and the strains issuing from RTG to mate. This is a phenotypic indicator of the MATa/MATα diploid character of the cells issuing from RTG.

Phenotypic Recombination Test.

To phenotypically characterize the recombinant nature of cells issuing from RTG, cell growth was examined on various selective media indicating the genotype of markers carried by the AND1702 parental strain (Arginine dropout, Histidine dropout, Leucine dropout, Methionine dropout). As this strain is heterozygous for arg4-RV and arg4-Bgl markers preventing cell growth on a medium lacking arginine (Arginine dropout), formation by recombination of RTG cells carrying an ARG4 allele allows the cells to grow on this medium. As strain AND1702 in the heterozygous state also carries the alleles his3Δ200/HIS3, his4B::LEU2/HIS4, and met15Δ0/MET15, its phenotype is [HIS+ LEU+ MET+] among others. The recombinant nature of the RTG cells may be revealed by the loss of one of these prototrophies ([his−]=his3Δ200/his3Δ200 or his4B::LEU2/his4B::LEU2, [leu−]=HIS4/HIS4, [met−]=met15Δ0/met15Δ0).

Phenotypic Test on Tetrads Obtained by Sporulation of RTG Diploids

The recombinant nature of RTG cells may also concern the loss of heterozygosity of a genetic marker with no change of phenotype. For example, an RTG cell may become MET15/MET15 by recombination, but will remain prototrophic for methionine as was the diploid parental strain AND1702. To detect these events, the phenotype of tetrads issuing from RTG diploids was analyzed on Arginine-DO, Histidine-DO, Leucine-DO, and Methionine-DO media to observe the segregation of genetic markers. The mating type of the cells was also determined using the method described above.

Genotype Analysis of Cells Issuing from RTG by NGS Sequencing

The genomes of the parental yeasts ORT7219, ORT7221, and AND1702, and of the cells issuing from RTG AND1708, AND1709, AND1710, AND1711, AND1712, AND1720, AND1733, AND1734, AND1735, AND1736, AND1737, AND1738, AND1739, AND1740, AND2711, AND2907, AND2642, AND2652, and AND2658, were sequenced by the NGS (Next-Generation Sequencing) method (NGS platform of the Institut Curie, Paris, France). For haploid strains ORT7219 and ORT7221, a genomic DNA fragment library was produced and sequenced using the paired-end methodology (50+35 nt) on SOLiD v4 sequencers according to the protocols of the vendor "Life Technologies". For haploid strains AND1710-1A, AND1710-1B, AND1710-1C, and AND1710-1D, a genomic DNA fragment library was constructed and sequenced using the paired-end methodology (50+35 nt) on SOLiD V5500 sequencers according to the protocols of the vendor "Life Technologies". For diploid strains AND1702, AND1708, AND1709, AND1710, AND1711, AND1712, AND1720, AND1733, AND1734, AND1735, AND1736, AND1737, AND1738, AND1739, and AND1740, Mate-pair libraries (50+50 nt) were constructed from genomic DNA preparations and sequenced on the SOLiD v4 sequencers of the NGS platform of the Institut Curie, according to the protocols of the vendor "Life Technologies". Strains AND2711, AND2907, AND2642, AND2652, and AND2658 of the Paired-end libraries (100+100 nt) were created from genomic DNA preparations and sequenced on the NGS platform of the Institut Curie on a HiSeq 2500 sequencer, according to the protocol of the vendor "Illumina".

Bioinformatic Analysis of NGS Sequencing Data

To determine the polymorphisms contributed by the haploid parental strains ORT7219 and ORT7221, the sequences from NGS were aligned with the sequence of the reference genome S288C using the Bioscope software (Life Technologies). The version of the reference sequence used (R64) is available on the "*Saccharomyces* Genome Database" (SGD) website (http://downloads.yeastgenome.org/sequence/S288C_reference/genome_releases/S288C_reference_genome_R64-1-1_20110203.tgz). The entry numbers for the 16 chromosomes and the mitochondrial genome are: Chromosome (Chr.) I: NC_001133: Chr. II: NC_001134; Chr. III: NC_001135; Chr. IV: NC_001136; Chr. V: NC_001137; Chr. VI: NC_001138; Chr. VII: NC_001139; Chr. VIII: NC_001140; Chr. IX: NC_001141; Chr. X: NC_001142; Chr. XI: NC_001143; Chr. XII: NC_001144; Chr. XIII: NC_001145; Chr. XIV: NC_001146; Chr. XV: NC_001147; Chr. XVI: NC_001148; and Mitochondrial Chr.: NC_001224. The list and coordinates of the SNPs (Single Nucleotide Polymorphisms) between the parental strains ORT7219 (S288C) and ORT7221 (SK) were established using the Bioscope "Find SNP" tool. The NGS sequences of the diploid cell AND1702, the cells issuing from RTG, and the four spores of the tetrad AND1710-1 were aligned with the reference genome sequence SGD using the Lifescope software (Life Technologies). To determine the genotype of each of the sequenced strains, the reads overlapping polymorphic positions within the established list of SNPs were selected using the "IntersectBED" tool of BEDTools (Quinlan et al., 2010). Then each read was associated with the polymorphism(s) it covers and the position of the polymorphism(s) in the read was calculated. The base for this position was then extracted and compared with the bases found at this position in the parental strains ORT7219 and ORT7221. At each polymorphic position, reads having the S288C allele, SK1 allele, or some other allele were counted. The SNP was declared monoallelic of S288C origin if the S288C allele was represented in more than 82% of the reads. It was declared to be monoallelic of SK1 origin if the SK1 allele was represented in more than 68% of the reads, and declared to be biallelic if the SK1 allele was represented in 18 to 68% of the reads or if the S288C allele was represented in 32 to 82% of the reads. The map of the polymorphic positions was then plotted using the R software environment (http://www.r-project.org) for each sample analyzed. The genotype of each polymorphic position was indicated by a color: black for monoallelic S288C, medium gray for monoallelic SK1, and light gray for biallelic. For all samples sequenced, coverage by position was calculated using the tool "genomeCoverageBed" of BEDTools. The 100 nt+100 nt reads from the Illumina sequencer were aligned with the reference genome (SGD) using the BWA software.

Results

Phenotypic Analyses

Selection of Recombinant RTG Cells

Six independent colonies (strains AND1708, AND1709, AND1710, AND1711, AND1712, and AND1720) issuing from RTG (parent AND1702, Protocol 2 for selecting cells prototrophic for arginine) as well as four "mother (M) and daughter (D)" RTG pairs (AND1733(M)-AND1734(D), AND1735(M)-AND1736(D), AND1737(M)-AND1738(D), and AND1739(M)-AND174(D)) issuing from RTG (parent AND172, Protocol for isolation by micromanipulating mother/daughter cells after the first cell division) were selected for genotyping. The diploid nature of these strains was confirmed by two phenotypic tests: absence of crosses with test haploid cells of mating sign MATa (RT3805) and MATα (ORT3806), and ability to enter sporulation and form tetrads with four viable spores (below). The phenotype of RTG cells for heterozygous markers (ARG, HIS, LEU, MET) is shown in Table 3 below.

TABLE 3

Phenotype of RTG cells

| Strain | ARG-DO | HIS-DO | LEU-DO | MET-DO | MATa test cells | MATα test cells |
|---|---|---|---|---|---|---|
| AND1702 | − | + | + | + | − | − |
| AND1708 | + | − | + | + | − | − |
| AND1709 | + | + | + | − | − | − |
| AND1710 | + | − | + | + | − | − |
| AND1711 | + | − | + | + | − | − |
| AND1712 | + | − | + | + | − | − |
| AND1720 | + | + | + | − | − | − |
| AND1733 | + | − | + | + | − | − |
| AND1734 | − | − | − | + | − | − |
| AND1735 | − | − | + | + | − | − |
| AND1736 | − | + | + | + | − | − |
| AND1737 | − | + | − | + | − | − |
| AND1738 | − | − | + | + | − | − |
| AND1739 | − | + | + | + | − | − |
| AND1740 | − | − | + | + | − | − |
| AND2711 | − | − | + | + | − | − |
| AND2907 | − | − | + | + | − | + |
| AND2642 | − | + | + | − | − | − |
| AND2652 | − | − | + | + | − | − |
| AND2658 | − | − | + | + | − | − |

None of the cells crossed with the MATa and MATα test cells, and therefore remained diploid. Out of all the sequenced cells issuing from RTG, seven became prototrophic for arginine (AND1708, AND1709, AND171, AND1711, AND1712, AND1720, and AND1733), nine became auxotrophic for histidine (AND1708, AND171, AND1711, AND1712, AND1733, AND1734, AND1735, AND1738, and AND1740), two became auxotrophic for leucine (AND1734 and AND1737), and two became auxotrophic for methionine (AND1709 and AND1720). This illustrates the phenotypic diversity of cells issuing from RTG and is the result of recombination events.

Identification of RTG Cell Genotype by Tetrad Analysis

To observe the segregation of genetic markers of RTG cells, these cells were sporulated and ten tetrads were dissected and analyzed. In 13 of 14 cases (AND1708, AND1709, AND1710, AND1712, AND1720, AND1733, AND1734, AND1735, AND1736, AND1737, AND1738, AND1739, and AND1740), tetrads with four viable spores were obtained, confirming the diploid nature of these RTG cells and indicating the absence of lethal mutations in the genome of these RTG diploids. For AND1711, the tetrads dissected had only two viable spores, reflecting the presence of an aneuploidy detected by analyzing the depth of sequence coverage of the reads and confirmed by Southern blot. This aneuploidy concerned the loss of a copy of 170 kb of one end of Chr. XVI, associated with a gain of a copy of 110 kb of Chr. V. Segregation of genetic markers in the dissected tetrads clarified the genotype of the markers of each diploid as shown in Table 1.

Bioinformatic Analysis The genome of parental haploids ORT7219 and ORT7221, the genome of the hybrid diploid AND1702, and the genome of RTG cells AND1708, AND1709, AND1710, AND1711, AND1712, AND1720, AND1733, AND1734, AND1735, AND1736, AND1737, AND1738, AND1739, and AND1740 were sequenced by NGS and the reads were analyzed using the methods described above.

Primary Analysis of Sequencing Data

For each sample, more than 60 million NGS reads were obtained with homogeneous coverage (number of reads per position) over the entire genome of more than 100×. The average coverage per sample is given in Table 4.

TABLE 4

Average coverage index for each sample sequenced, after removal of PCR duplicates

| Sample | Alignment method | Average coverage index |
|---|---|---|
| ORT7219 | Bioscope | 192X |
| ORT7221 | Bioscope | 141X |
| AND1702 | Lifescope | 43X |
| AND1708 | Lifescope | 95X |
| AND1709 | Lifescope | 174X |
| AND1710 | Lifescope | 181X |
| AND1711 | Lifescope | 186X |

TABLE 4-continued

Average coverage index for each sample sequenced, after removal of PCR duplicates

| Sample | Alignment method | Average coverage index |
|---|---|---|
| AND1712 | Lifescope | 189X |
| AND1720 | Lifescope | 179X |
| AND1733 | Lifescope | 16X |
| AND1734 | Lifescope | 27X |
| AND1735 | Lifescope | 80X |
| AND1736 | Lifescope | 69X |
| AND1737 | Lifescope | 53X |
| AND1738 | Lifescope | 28X |
| AND1739 | Lifescope | 15X |
| AND1740 | Lifescope | 21X |
| AND1710-1A | Lifescope | 124X |
| AND1710-1B | Lifescope | 111X |
| AND1710-1C | Lifescope | 90X |
| AND1710-1D | Lifescope | 120X |
| AND2711 | BWA | 90X |
| AND2907 | BWA | 89X |
| AND2642 | BWA | 89X |
| AND2652 | BWA | 90X |
| AND2658 | BWA | 91X |

Identification of Polymorphisms Differentiating Parental Haploids

Analysis of NGS sequences of strain 0RT7219 compared with the SGD reference sequence led to identifying 115 SNPs. Analysis of NGS sequences of strain 0RT7221 compared with the SGD reference sequence led to identifying 65,134 SNPs. Of these, 63,901 SNPs were selected for genotyping the NGS reads of the AND1702 hybrid diploid and the cells issuing from RTG. The physical distance between SNPs varies between 2 and 38,036 nucleotides with a median of 96 nucleotides and an average of 187 nucleotides.

Genotype of RTG Cells

All the parental polymorphisms were found in the sequenced cells. Each RTG strain was a carrier of monoallelic SNPs and biallelic SNPs in varying numbers. The results reported in Table 5 below show that 61 to 89% of the SNPs are biallelic, confirming the diploid nature of these cells issuing from RTG. The other SNPs are monoallelic, corresponding in 6 to 26% of the cases to the S288C allele and corresponding in 1 to 18% of the cases to the SK1 allele, meaning that on the average 1700 of the SNPs are found in the monoallelic state. The presence of a single allele at these monoallelic positions indicates a loss of heterozygosity (LOH) which may reflect either the presence of two homologous chromosomes carrying the same allele or a loss of the chromosomal region in one of the homologous chromosomes. The analysis of coverage averaged over 1 kb of each chromosome shows that the monoallelic regions and heteroallelic regions have a uniform coverage index, which supports the hypothesis of two homozygous homologous chromosomes.

TABLE 5

Percentage loss of heterozygosity in different RTG strains

| strain | Length of incubation in KAc | Proportion of monoallelic positions S288C (%) | Proportion of monoallelic positions SK1 (%) | Proportion of biallelic positions (%) |
|---|---|---|---|---|
| AND1708 | 6 h | 25.1 | 2.9 | 71.8 |
| AND1709 | 5 h | 13.3 | 13.4 | 73.1 |
| AND1710 | 5 h | 13.4 | 12.0 | 74.3 |
| AND1711 | 5 h | 14.5 | 13.7 | 71.6 |
| AND1712 | 5 h | 8.9 | 6.7 | 84.3 |
| AND1720 | 5 h | 12.5 | 9.2 | 78.1 |
| AND1733 | 5 h | 17.7 | 8.8 | 73.5 |
| AND1734 | 5 h | 9.5 | 16.6 | 73.9 |
| AND1735 | 5 h | 5.4 | 4.4 | 90.2 |
| AND1736 | 5 h | 4.1 | 5.4 | 90.6 |
| AND1737 | 8 h | 6.5 | 0.2 | 93.3 |
| AND1738 | 8 h | 0.2 | 6.4 | 93.3 |
| AND1739 | 8 h | 8.6 | 3.7 | 87.6 |
| AND1740 | 8 h | 4.0 | 8.2 | 87.8 |
| AND2711 | 4 h | 21.5 | 10.9 | 67.6 |
| AND2907 | 6 h | 26.8 | 19.7 | 53.5 |
| AND2642 | 8 h | 8.7 | 6.9 | 84.4 |
| AND2652 | 8 h | 11.6 | 9.0 | 79.3 |
| AND2658 | 8 h | 5.5 | 1.2 | 93.1 |

Maps of the state of the SNPs (biallelic, monoallelic of S288C origin or monoallelic of SK1 origin) of the analyzed RTG cells are illustrated in FIGS. 1 and 2. Cells isolated according to the above Protocol 2 are illustrated in FIG. 1. Cells isolated according to the above Protocol 3 are illustrated in FIG. 2 (mother and daughter cells from the same RTG event are grouped in the same figure, to paired comparisons of the two genotypes).

Figure 1A:
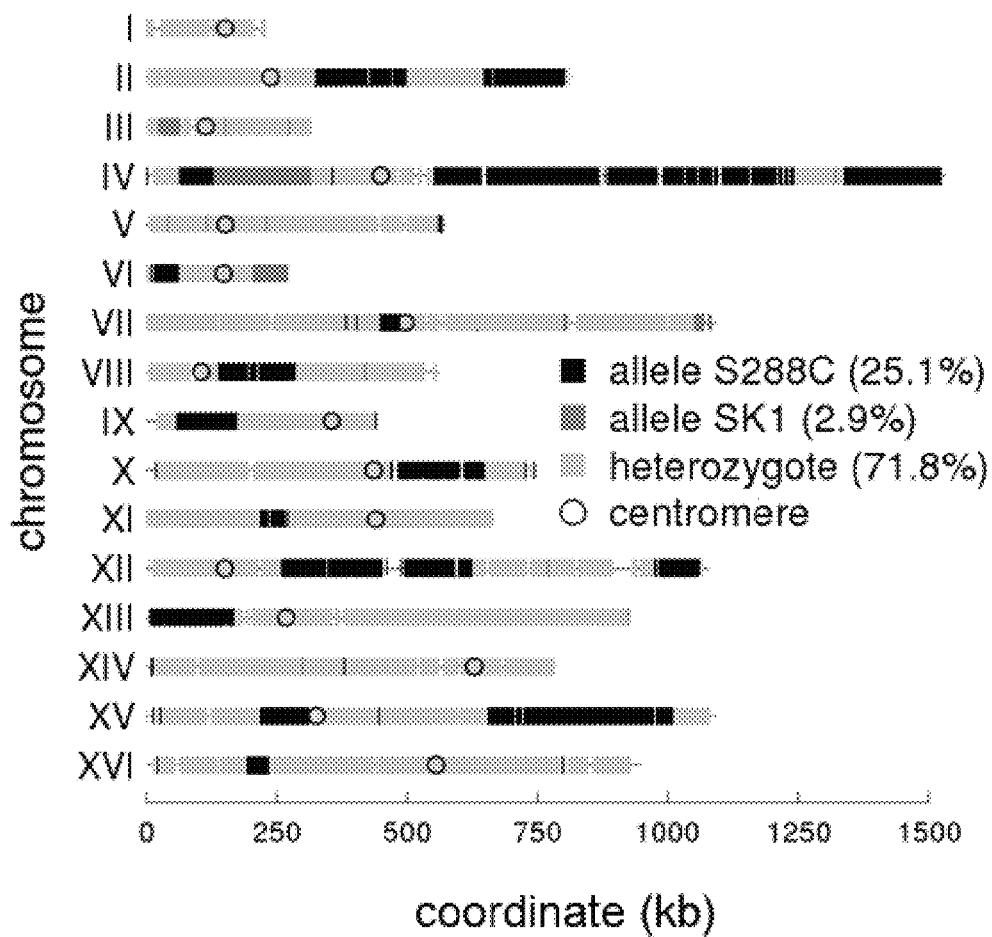
FIG. 1A: Genotype of the AND1708 RTG cell (21 monoallelic regions of greater than 20 kb; 34 junctions between monoallelic regions and biallelic regions, or between monoallelic regions of different alleles; size of the largest region of loss of heterozygosity: approx. 691 kb).
Figure 1B:
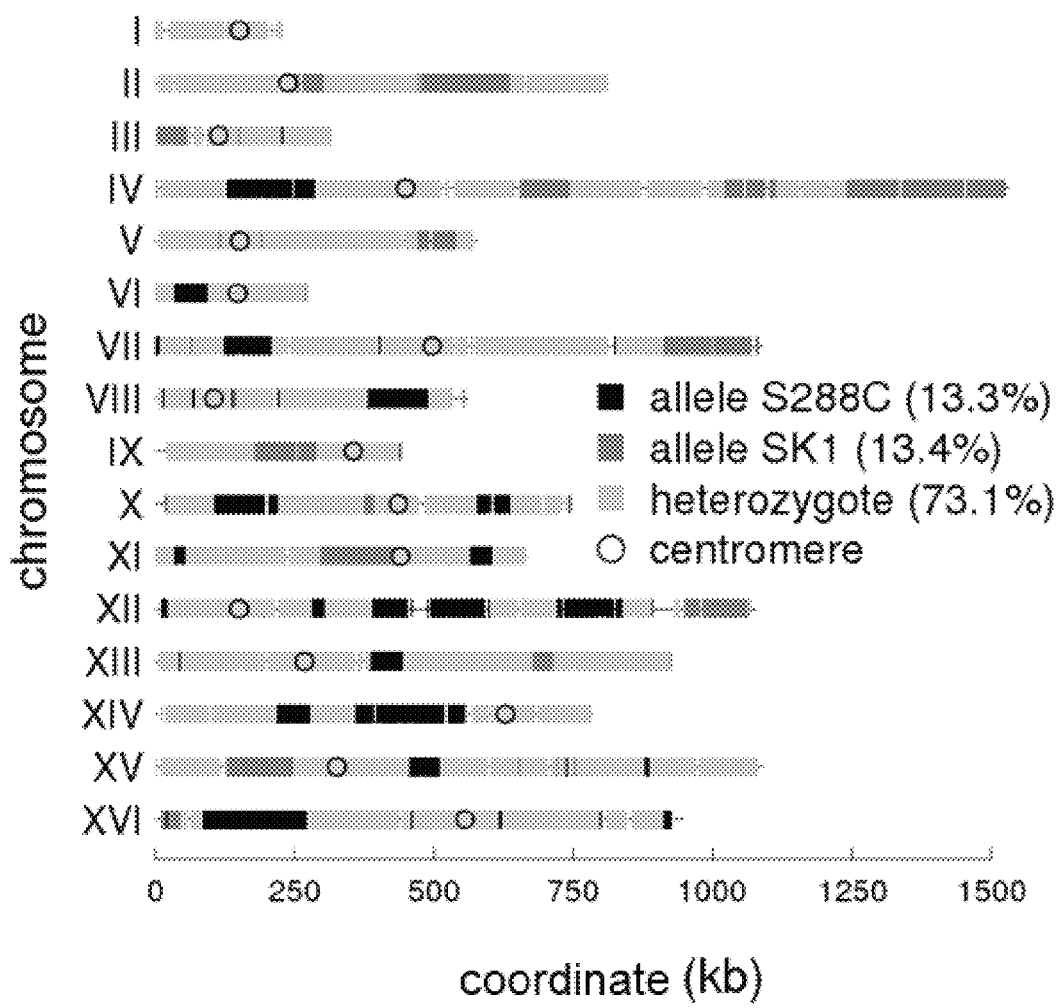
FIG. 1B: Genotype of the AND1709 RTG cell (29 monoallelic regions of greater than 20 kb; 53 junctions between monoallelic regions and biallelic regions, or between monoallelic regions of different alleles; size of the largest region of loss of heterozygosity: approx. 264 kb).
Figure 1C:
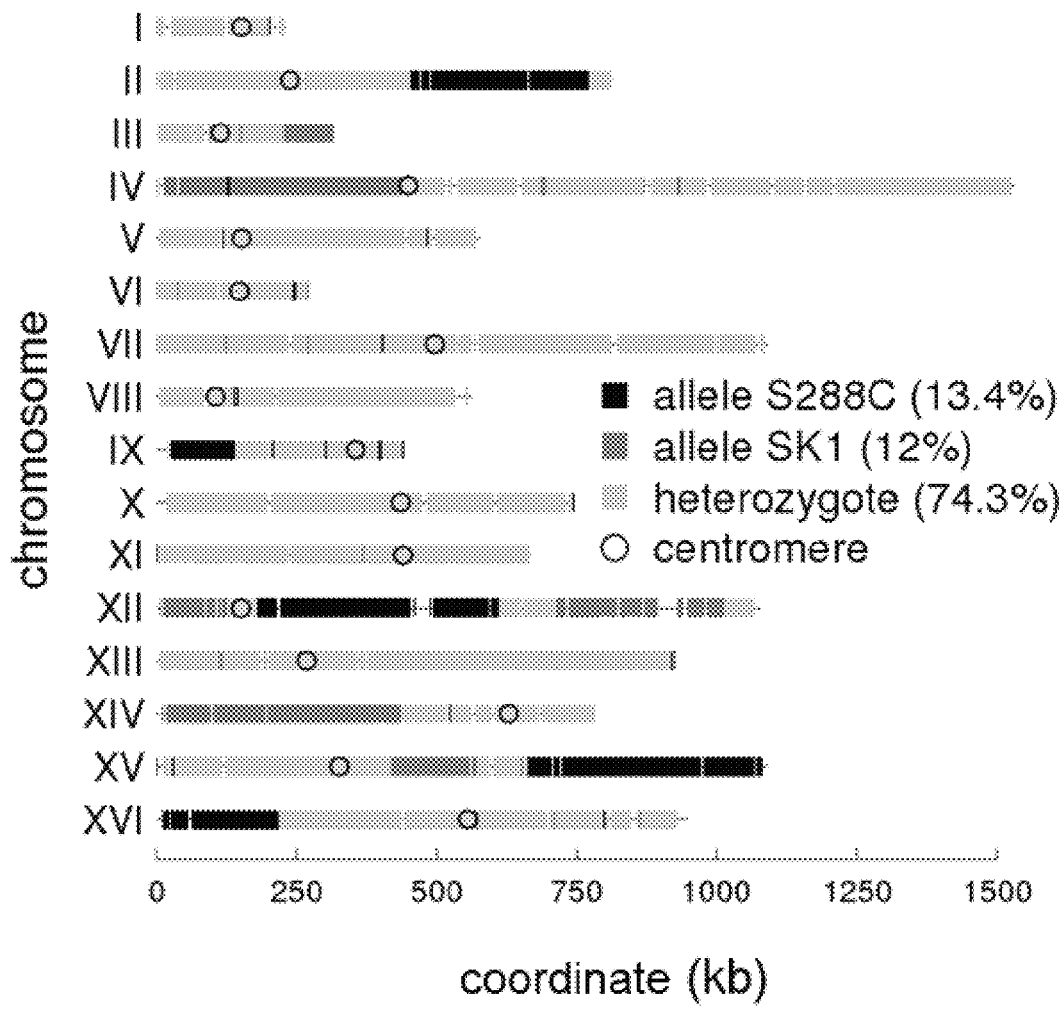
FIG. 1C: Genotype of the AND1710 RTG cell (11 monoallelic regions of greater than 20 kb; 15 junctions between monoallelic regions and biallelic regions or between monoallelic regions of different alleles; size of the largest region of loss of heterozygosity: approx. 431 kb).
Figure 1D:
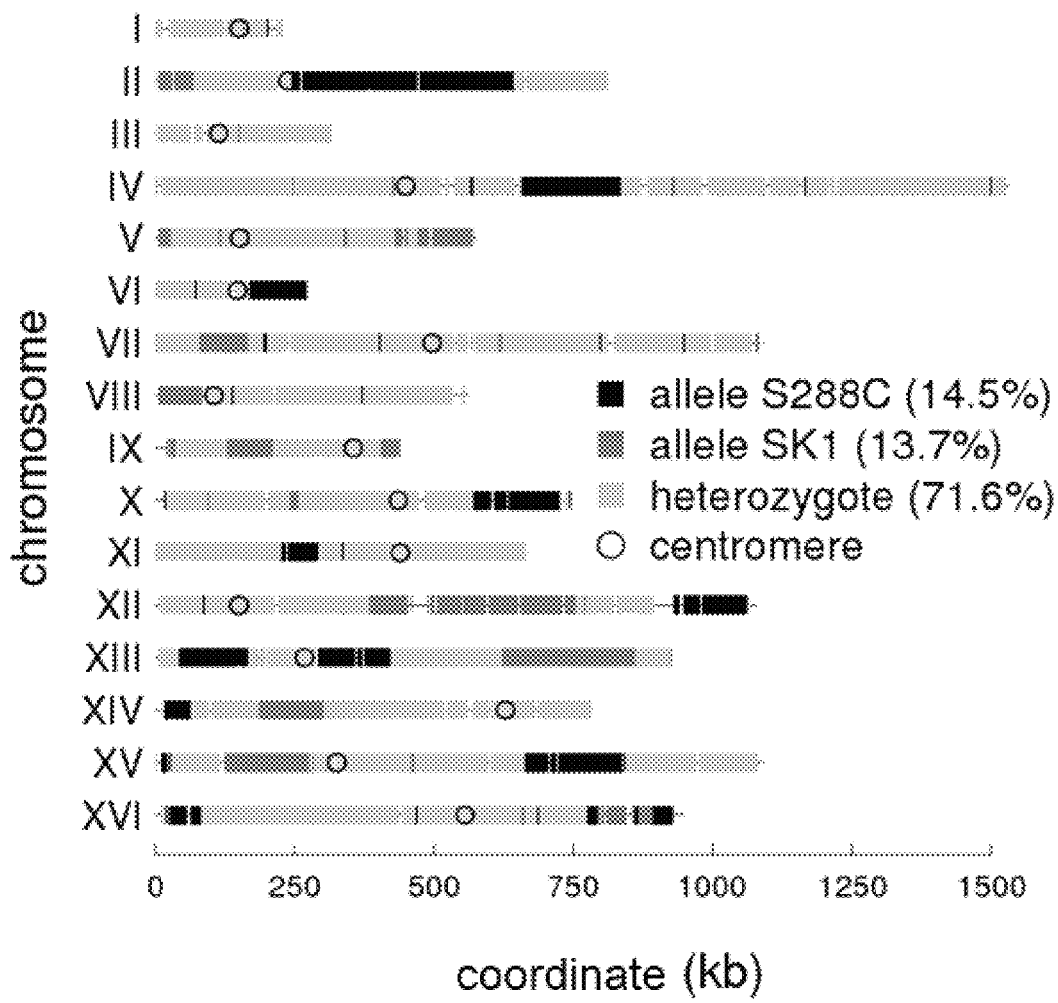
FIG. 1D: Genotype of the AND1711 RTG cell (25 monoallelic regions of greater than 20 kb; 38 junctions between monoallelic regions and biallelic regions or between monoallelic regions of different alleles; size of the largest region of loss of heterozygosity: approx. 398 kb).
Figure 1E:
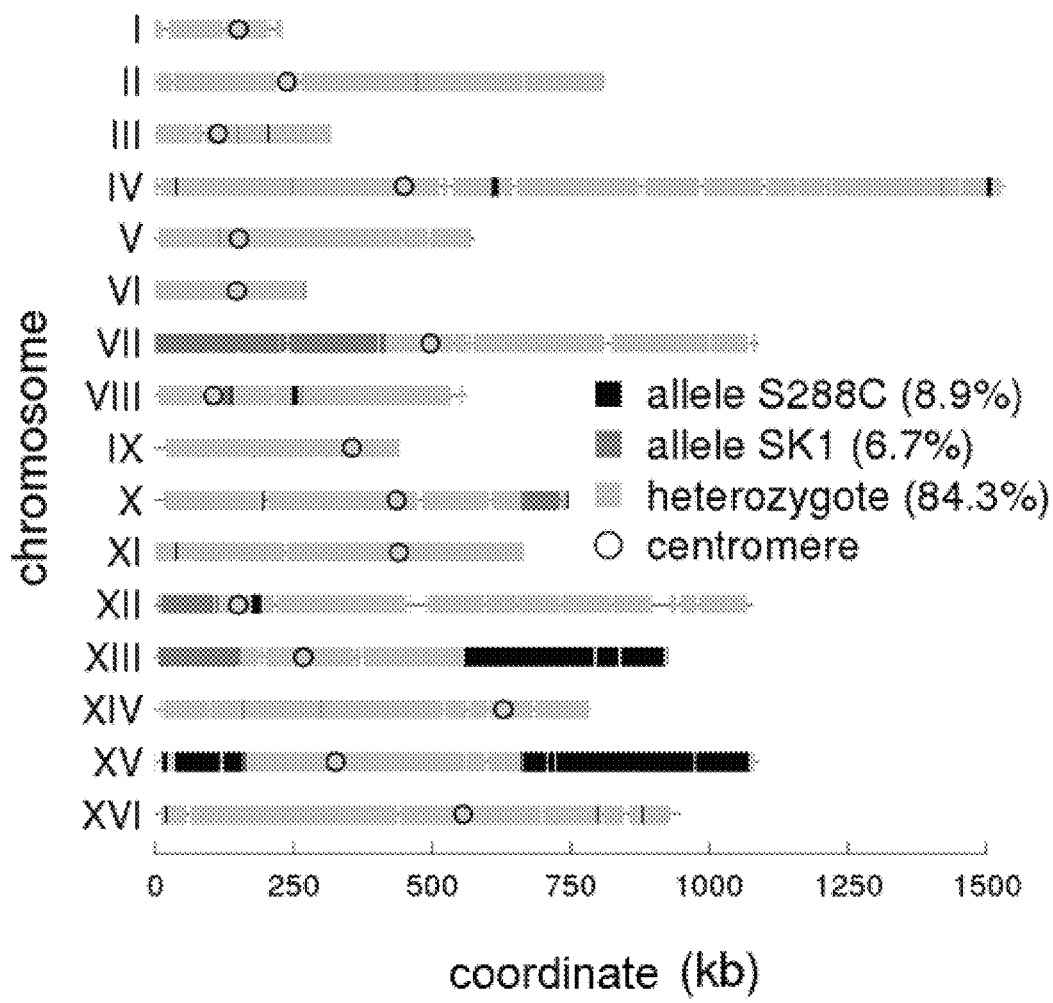
FIG. 1E: Genotype of the AND1712 RTG cell (7 monoallelic regions of greater than 20 kb; 7 junctions between monoallelic regions and biallelic regions or between monoallelic regions of different alleles; size of the largest region of loss of heterozygosity: approx. 415 kb).
Figure 1F:
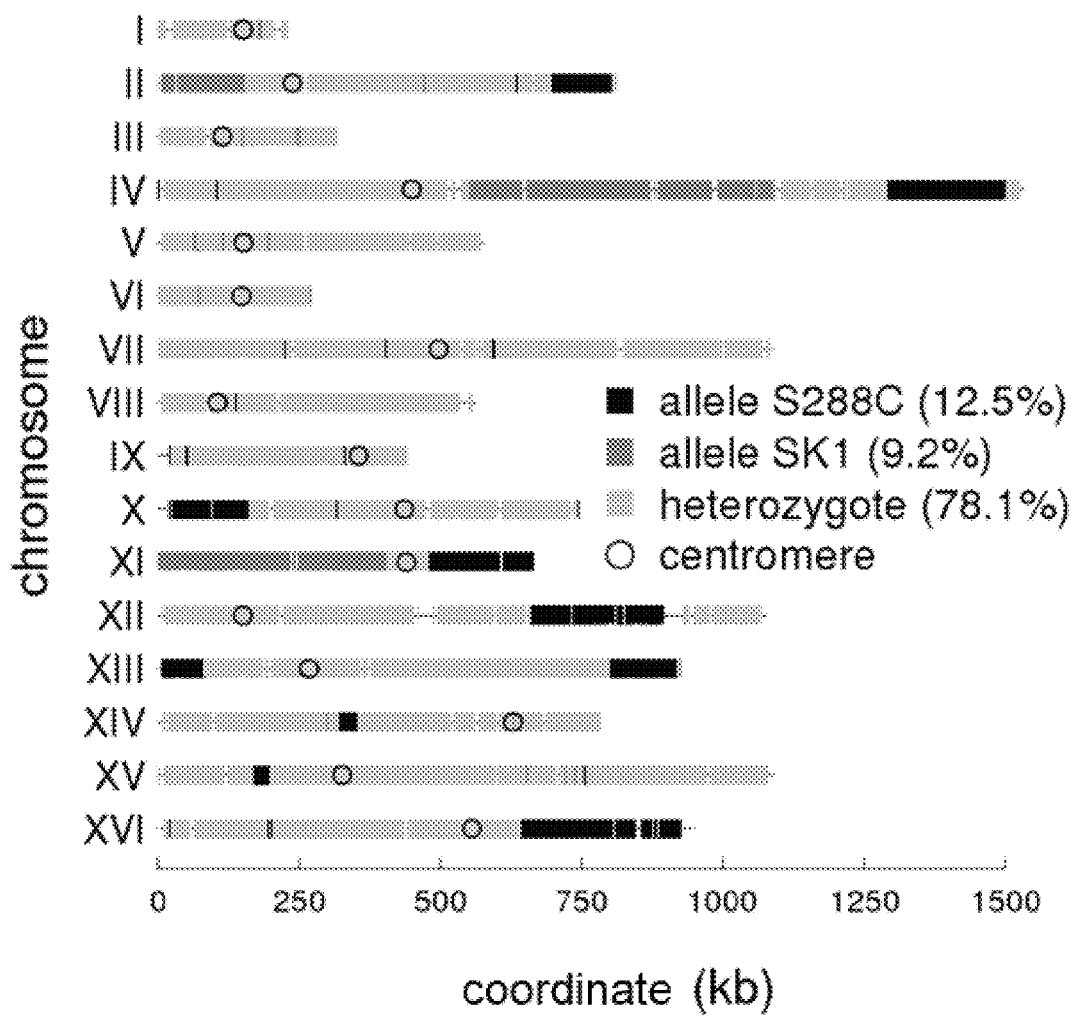
FIG. 1F: Genotype of the AND1720 RTG cell (13 monoallelic regions of greater than 20 kb; 18 junctions between monoallelic regions and biallelic regions, or between monoallelic regions of different alleles; size of the largest region of loss of heterozygosity: approx. 537 kb).
Figure 2A:
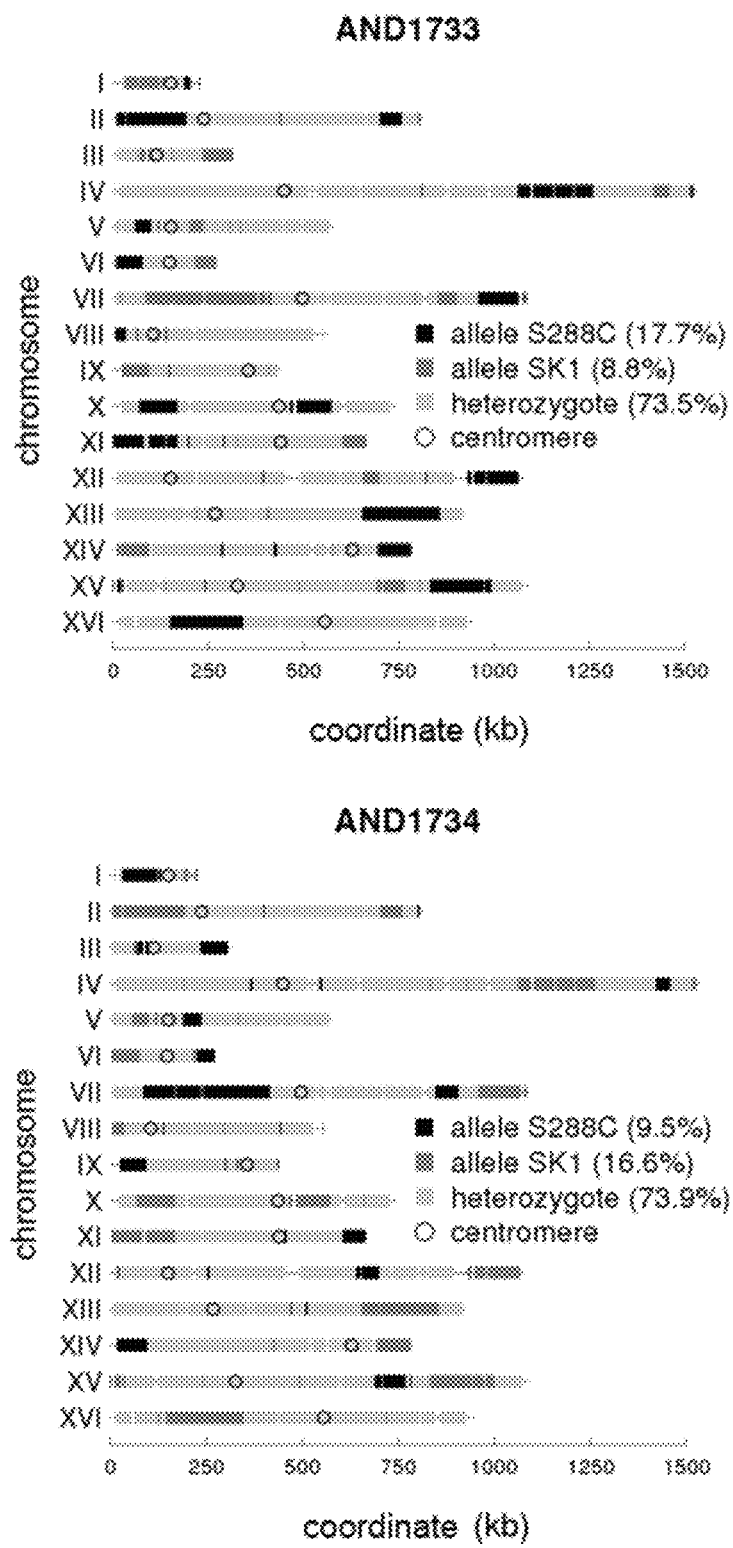
FIG. 2A: Genotype of AND1733 (mother cell) and AND1734 (daughter cell) RTG cells (29 monoallelic regions of greater than 20 kb; 45 junctions between monoallelic regions and biallelic regions, or between monoallelic regions of different alleles; size of the largest region of loss of heterozygosity: approx. 300 kb).
Figure 2B:
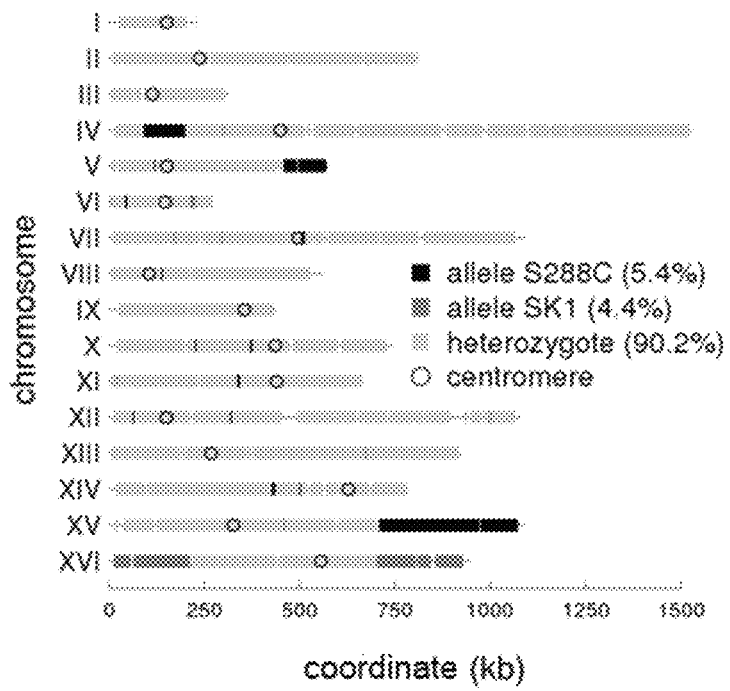
FIG. 2B: Genotype of AND1735 (mother cell) and AND1736 (daughter cell) RTG cells (5 monoallelic regions of greater than 20 kb; 6 junctions between monoallelic regions and biallelic regions, or between monoallelic regions of different alleles; size of the largest region of loss of heterozygosity: approx. 361 kb).
Figure 2B:
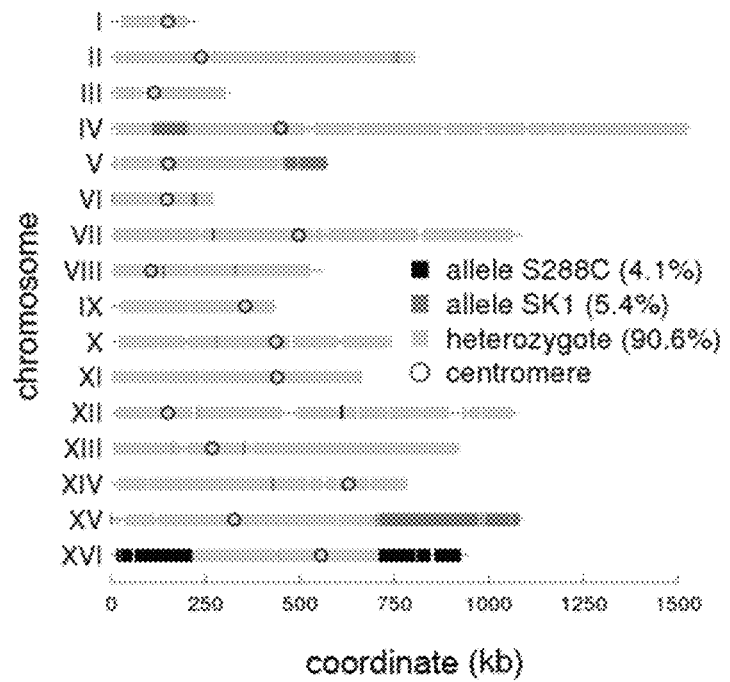
Figure 2C:
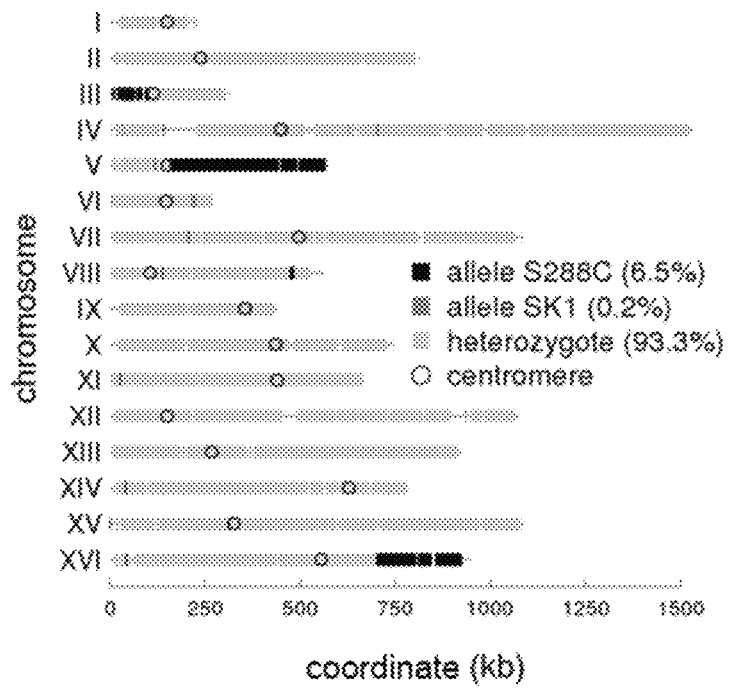
FIG. 2C: Genotype of AND1737 (mother cell) and AND1738 (daughter cell) RTG cells (3 monoallelic regions of greater than 20 kb; 3 junctions between monoallelic regions and biallelic regions, or between monoallelic regions of different alleles; size of the largest region of loss of heterozygosity: approx. 393 kb).
Figure 2C:
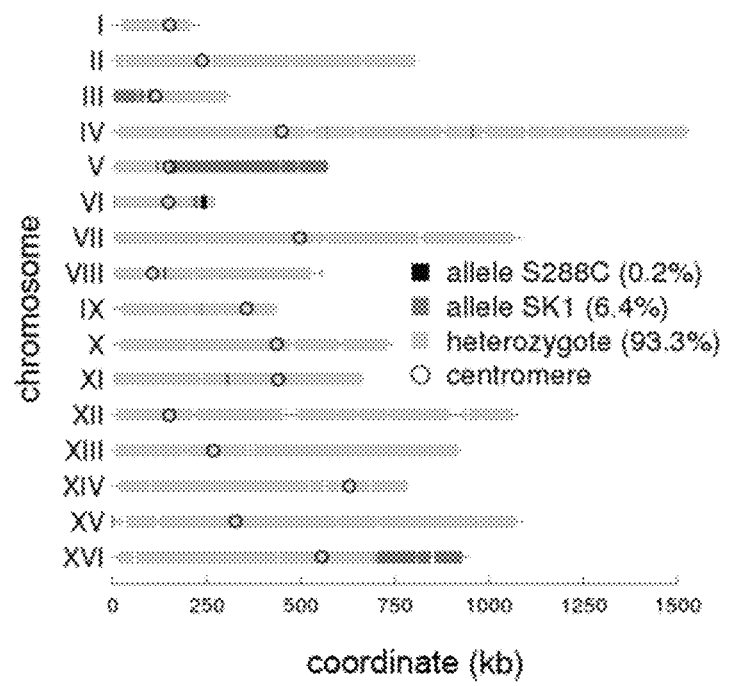
Figure 2D:
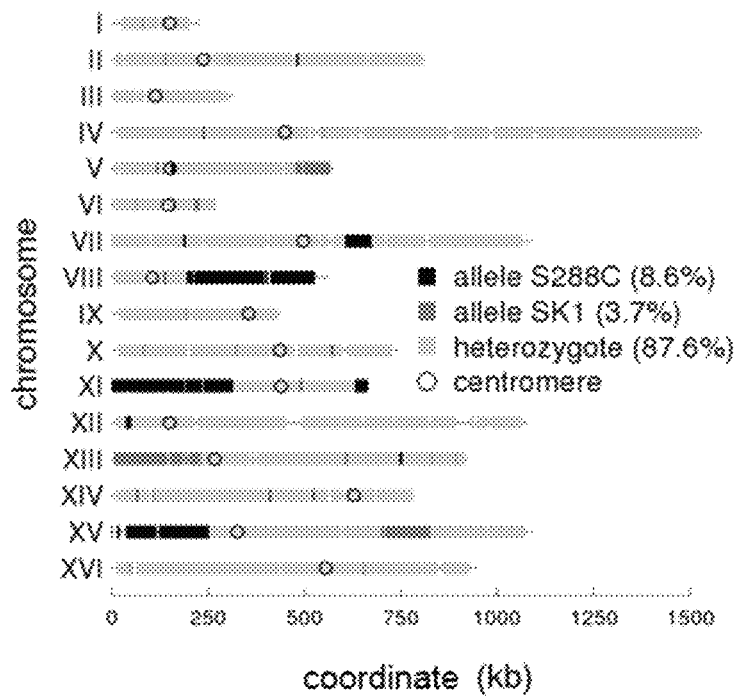
FIG. 2D: Genotype of AND1739 (mother cell) and AND1740 (daughter cell) RTG cells (8 monoallelic regions of greater than 20 kb; 10 junctions between monoallelic regions and biallelic regions, or between monoallelic regions of different alleles; size of the largest region of loss of heterozygosity: approx. 357 kb).
Figure 2D:
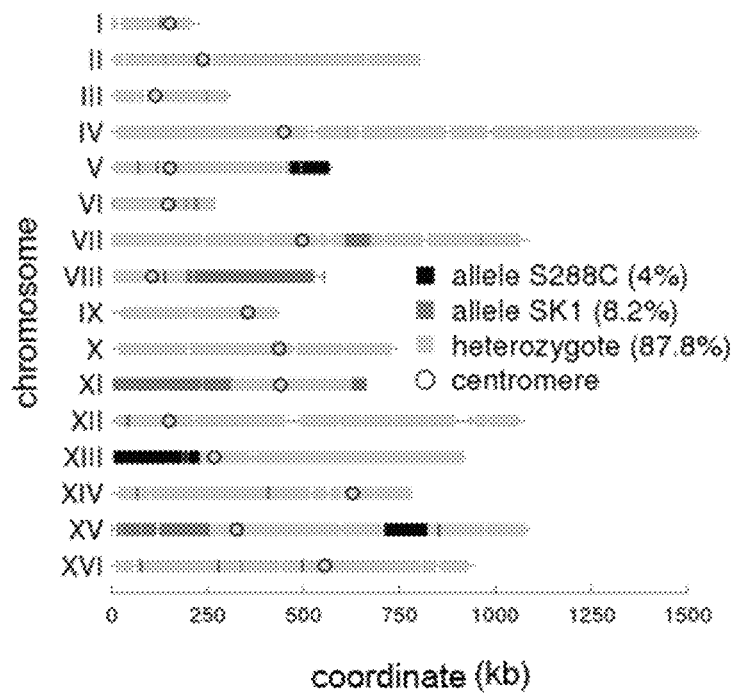

The genotype of these cells is very different. In most cases, each chromosome is composed of biallelic and monoallelic regions of varying sizes involving one or many SNP positions (from 1 nucleotide to close to 700 kb) of S288C and/or SK1 origin. The arrangement of the bi- and monoallelic regions, revealing the existence of localized recombination at the junction points, differs according to the cells. When considering only monoallelic regions of at least 20 kb, the number of recombinant junctions per chromosome varies from 0 to 7 and the total estimated number per cell is 34, 53, 15, 38, 7, 18, in the RTG strains AND1708 (FIG. 1A), AND1709 (FIG. 1), AND1710 (FIG. 1C), AND1711 (FIG. 1D), AND1712 (FIG. 1E), AND1720 (FIG. 1F), and is 45, 6, 3, 11 in the mother-daughter pairs AND1733-AND1734 (FIG. 2A), AND1735-AND1736 (FIG. 2B), AND1737-AND1738 (FIG. 2C), and AND1739-AND1740 (FIG. 2D). We note that (i) SNPs located near the centromeres remain biallelic, confirming mitotic segregation of sister chromatids in RTG, and (ii) the genotype of mother and daughter cells is complementary, being identical in biallelic regions and of opposite alleles in monoallelic regions. Unlike the isolation of individual RTG cells (Protocols 1 and 2), the method of isolating the mother and daughter pairs (Protocol 3) has the advantage of allowing analysis of phenotypes in a homogeneous context for biallelic SNPs.

Genotype Confirmation for the AND1710 Strain by Sequencing a Tetrad

Figure 3:
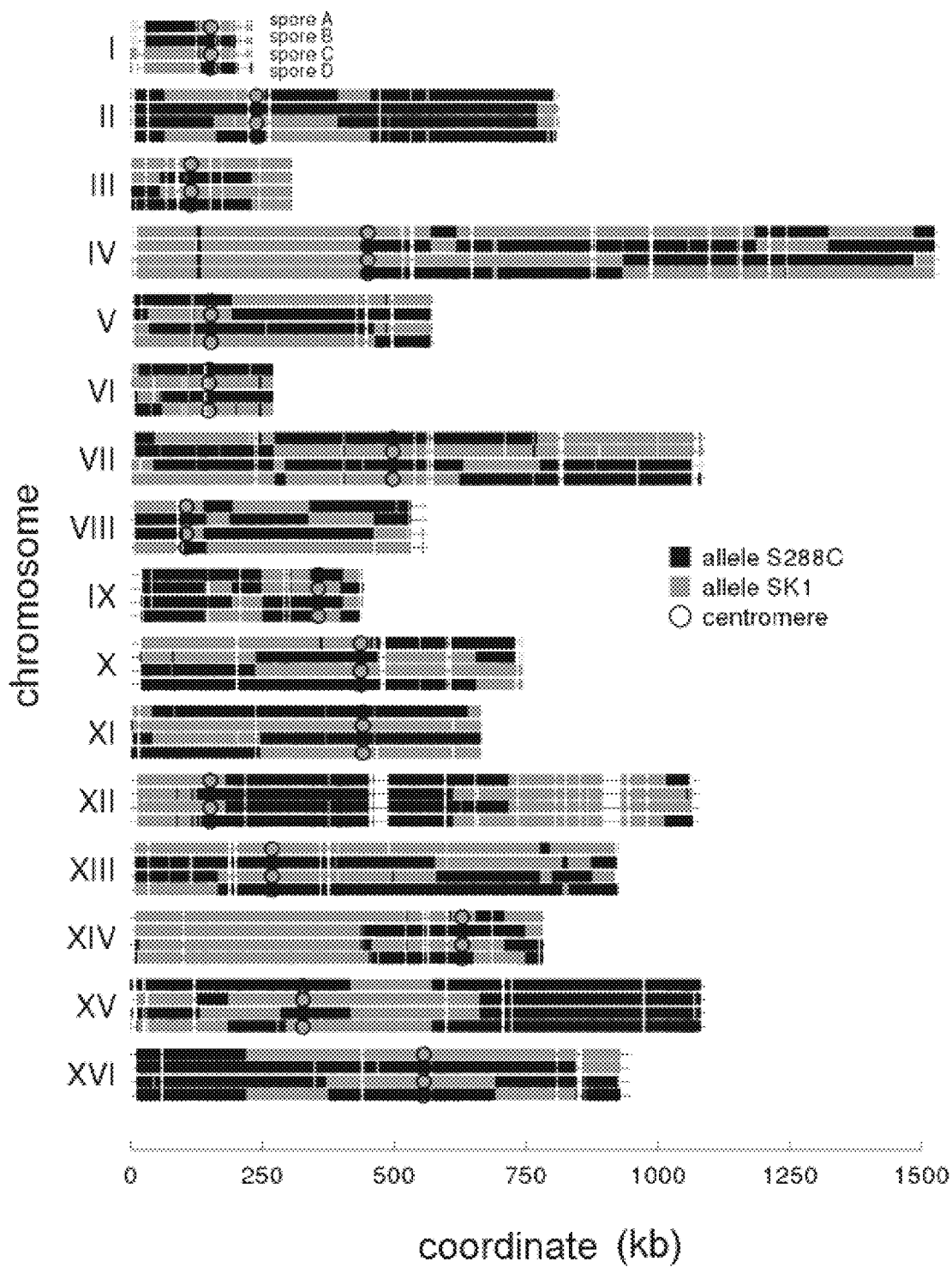
FIG. 3. Genotype of the four spores of the tetrad issuing from the AND1710 RTG cell. For each of the 16 chromosomes, the genotype of spores A, B, C and D of the tetrad is shown one below the other.

Four spores from a tetrad issuing from sporulation of the AND1710 RTG diploid were sequenced and the genotype of the polymorphism positions was determined. The polymorphism genotype of the four spores (A, B, C, D) of the tetrad is illustrated in FIG. 3.

For monoallelic regions of the AND1710 diploid, we observe that the four spores have the same allele of S288C or SK1 origin. The biallelic regions of the diploid segregate in two spores carrying the S288C allele and two spores carrying the SK1 allele, confirming the heterozygous nature of the diploid in these regions. The 15 recombinant junctions of the AND1710 RTG diploid are confirmed. Furthermore, additional recombination events (chr. VII, chr. VIII, and chr. IX (two cases)) associated with gene conversions were identified at the four short monoallelic regions of the AND1710 diploid. Other recombination events occurred during meiosis leading to the formation of this tetrad and the recombinant genotype was not present in the parental RTG diploid.

Repeating the RTG Process

To assess whether the RTG process could be repeated to increase genetic diversity, the inventors conducted two successive RTG cycles using the AND1735 strain (FIG. 4A) resulting from a first RTG cycle of the parental diploid AND1702 and analyzed by sequencing the evolution of the SNP markers. During the second RTG cycle, the AND2711 cell underwent another cycle of recombination as evidenced in a decrease in the overall level of heterozygosity (67.6% instead of 90.2%) and the appearance of new monoallelic regions of S288C or SK1 genetic background (FIG. 4B). Then, during the third RTG cycle, the AND2907 cell underwent another cycle of recombination as evidenced in an additional reduction in the overall level of heterozygosity (53.5% instead of 67.6%) and the appearance of new monoallelic regions of S288C or SK1 genetic background (FIG. 4C, Table 5). The RTG process can therefore be repeated to sequentially increase the genetic diversity of diploid cells.

RTG in Sporulation-Deficient AND2248 Diploid Cells

To assess whether the RTG process could be used to recombine the genome of sterile diploid cells, the inventors have constructed a diploid strain (AND2248) of S288C/SK1 hybrid genetic background, but carrying a deletion of the NDT80 gene in the homozygous state. Inactivation of the NDT80 gene leads to an absence of spore formation (hence the sterility phenotype), but does not prevent the diploid cells from entering the meiotic prophase. These cells stop their meiotic progression at a stage after the formation of Spo11-dependent DNA double-strand breaks but before the stage of reductional chromosome division (M1) (Chu & Herskowitz, 1998). The ndt80 ndt80 diploid cells thus arrested in the meiotic prophase remain viable and are able to return to vegetative growth via the RTG process (Dayani et al., 2011). Three strains isolated after RTG (Protocol 3) from the AND2248 mutant strain were sequenced. Maps of the SNPs of these strains (AND2642, AND2652, and AND2658) are illustrated in FIGS. SA-C, respectively. Their genotypes are recombinant and distinct (Table 5). The respective degrees of heterozygosity are 84.4%, 79.3%, and 93.1%, with the remainder of the genome carrying monoallelic positions of S288C or SK1 origin and the total number of recombinant junctions being 12, 24, and 5 per cell. The RTG method is therefore applicable to sterile strains capable of forming natural Spo11-dependent double-strand breaks.

Analysis of Variability of the RTG Cell Genotype

As RTG cells are usually diploid (except AND1711), the percentage decrease of heterozygosity per cell is accompanied by the appearance of homozygous regions of S288C or SK1 genotype. The variation in the heterozygosity and homozygosity percentage of the 19 strains issuing from an RTG process (Table 5) is illustrated in FIG. 6. The percentage of heterozygosity (S288C+SK1 biallelic genotype) varies between 93.3% (AND1738 and AND1739 issuing from Protocol 3) and 53.5% (AND2907) issuing from three RTG cycles. The proportion of S288C homozygous regions varies between 0.2% (AND1738) and 26.8% (AND2907). The proportion of SK1 homozygous regions varies between 0.2% (AND1737) and 19.7% (AND2907). The size of these homozygous regions can be short, involving only a few adjacent SNPs markers, or very large involving large chromosomal regions. The total number of recombinant junctions per RTG cell, estimated by taking into account only the recombinant regions at least 20 kb in length, varies between 3 (AND1737) and 53 (AND1709). The RTG method therefore allows creating a population of diverse recombinant cells that simultaneously carry heterozygous and homozygous regions for one of the genotypes of the hybrid parent and of varying sizes, in both the fertile and sterile cells.

Example of Mapping the Auxotrophic Character of Methionine and Leucine

To assess the performance of the RTG method in identifying and locating a single phenotypic trait, the inventors analyzed the genotype and phenotype of RTG cells for growth in the absence of methionine. The S288C strain has a deletion of the MET15 gene (met15Δ0). Thus, the parental diploid carries the MET15/met15Δ0 biallelic trait. A recombinant diploid auxotrophic for methionine must have monoallelic markers of the S288C allele around the MET15 locus (chr. XII). Conversely, the diploid prototrophic for methionine may carry monoallelic markers of the SK1 allele or biallelic markers around the MET15 locus, but never monoallelic markers of the S288C allele. It is thus possible to map the chromosomal regions associated with the phenotype by looking for the SNP positions where one or two alleles among {S288C-SK1-biallelic} are found specifically and exclusively associated with one or the other of the phenotypes. For this, the inventors examined the growth of haploid parental cells ORT7221 and ORT7219, of the hybrid diploid AND1702 and the RTG cells AND1708, AND1709, AND1710, AND1711, AND1712, AND1720, AND1733, AND1734, AND1735, AND1736, AND1737, AND1738, AND1739, and AND1740 on the methionine-DO medium. In accordance with their genotypes (Table 1), the biallelic diploid cells MET15/met15Δ0 (hybrid parents AND1702, RTG AND1708, AND1712, AND1733, AND1734, AND1735, AND1736, AND1737, AND1738, AND1739, and AND1740) and the monoallelic diploids MET15/MET15 (RTG AND1710 and AND1711) were capable of growing in the absence of methionine while the monoallelic diploid cells met15Δ0/met15Δ0 (RTG AND1709 and AND1720) were unable to grow in the absence of methionine. To determine the region of the genome carrying this trait, the inventors grouped the RTG cells into two categories: prototrophic (RTG AND1708, AND1710, AND1711, AND1712, AND1733, AND1734, AND1735, AND1736, AND1737, AND1738, AND1739, and AND1740) and auxotrophic (RTG AND1709 and AND1720), then compared their genotypes in order to identify regions of the genome where the alleles found in prototrophic individuals are found exclusively in this category, as well as the alleles found in auxotrophic individuals are found exclusively in this category. With only two samples in the auxotrophic category, this method identifies the trait in a very limited number of candidate regions (six regions and a few isolated SNPs) (FIG. 7A) including the desired region of the MET15 gene. Using a bioinformatics simulation where the two MET15/MET15 homozygous samples (AND1710 and AND1711) were artificially rendered homozygous met15Δ0/met15Δ0 by inversion of the alleles of the monoallelic locus, the inventors were able to show that by balancing the number of samples in the two categories, one could easily reduce the number of candidate regions to 1, including the MET15 gene. In this example, the identified region is about 40 kb.

Studying a larger number of RTG cells has the effect of reducing the size of the candidate region.

Similarly, the inventors analyzed the genotype and phenotype of the RTG cells for growth in the absence of leucine. The two parental strains have a mutation of the LEU2 locus (leu2Δ0 for the S288C parent and leu2::hisG for the SK1 parent, Chr. III). However, the SK1 parent has a wild-type copy of the LEU2 gene inserted into a neighboring locus (his4B::LEU2 marker on chromosome III). After RTG, this leads to obtaining the monoallelic diploids his4B::LEU2/his4B::LEU2 (AND1708, AND1733, and AND1738), the biallelic diploids his4B::LEU2/HIS4 (AND1709, AND1710, AND1711, AND1712, AND1720, AND1735, AND1736, AND1739, and AND1740), constituting the group of RTG cells prototrophic for leucine, and the monoallelic diploids HIS4/HIS4 (AND1734 and AND1737) constituting the group auxotrophic for leucine. Here, with only two samples in the auxotroph category, mapping the growth phenotype on leucine-DO medium leads to the identification of only two candidate regions (FIG. 7B), including the wanted region of the LEU2 and HIS4 gene.

These are examples of mapping a Mendelian trait by sequencing a small number of RTG cells, applicable for sterile hybrids.

Example of Improving a Quantitative Trait by the RTG Method

To assess the performance of the RTG method in identifying and locating quantitative traits, the inventors examined growth, at temperatures of 30° C. and 40° C., of the haploid parental cells ORT7221 and ORT7219, of the hybrid diploid AND1702, and of RTG cells AND1708, AND1709, AND1710, AND1712 and AND1720, AND1733, AND1734, AND1735, AND1736, AND1737, AND1738, AND1739, and AND1740. The results illustrated in FIG. 8 show that the haploid parental cells ORT7235 and ORT7236 have little growth at 40° C. Instead, the AND1702 hybrid cell exhibits the hybrid vigor phenomenon (heterosis) because it grows better at this temperature than each parent. The cells issuing from RTG exhibit a variable phenotype, growing more or less well at 40° C. In particular, the RTG cells AND1708, AND1710, AND1712, AND1735, AND1736, and AND1737 are more thermotolerant than the parental cells and are at least as thermotolerant as the hybrid diploid cell AND1702. Also, the inventors examined cell growth in the presence of sodium arsenite (1.5 mM NaAsO$_2$). The growth of the RTG cells is variable. For example, the AND1736 and AND1737 cells are more resistant than the parental diploid cell AND1702, while the AND1735 and AND1738 cells are more sensitive.

These are two examples of improving a quantitative trait of interest. The number and location of causal polymorphic markers can be deduced from comparative analysis of the genotype of the cells obtained by sequencing.

REFERENCES

Acquaviva L., et al., (2013). Science, 339, 215-218.
Albers et al., (1996), Applied and Environmental Biology, 62:3187-3195.
Becker and Guarente, Methods Enzymol., (1991) 194, 182-7.
Ben-Ari et al., (2006). PLoS Genet. 2(11): e195.
Chu and Herskowitz (1998) Mol. Cell 1, 685-696.
Dayani et al., (2011). PloS Genet. 7(5):e1002083.
De Massy et al., (1994). Proc. Nat. Acad. Sci USA, 91, 11929-11933.
Esposito and Esposito (1974). Proc. Nat. Acad. Sci USA, 71 (8), 3172-3176.
Greig (2007). PLoS Genet., 3(2): e21.
Herman and Roman (1963). Genetics, 48, 255-261.
Honigberg and Esposito (1994). Proc. Nat. Acad. Sci USA, 91, 6559-6563.
Honigberg and Purnapatre (2003). J. Cell Sci. 116, 2137-2147.
Kane and Roth (1974). Bacteriol, 118(1), 8-14.
Kassir and Simchen (1991). Meth. Enzymol. 194, 94-110.
Keeney (2001). Curr. Top. Dev. Biol. 52, 1-53.
Mortimer and Johnston (1986). Genetics, 113(1), 35-43.
Nicolas et al., (1989). Nature, 338, 35-39.
Quinlan et al., (2010). Bioinformatics, 15; 26(6), 841-2.
Rainieri et al., (1999). S. Afr. J. Enol. Vitic., Vol. 20, No. 2.
Rocco et al., (1992). Proc. Nat. Acad. Sci USA, 89, 12068-72.
Smith and Nicolas (1998). Curr. Opin. Genet. Dev. 8(2), 200-211.
Sherman (1991). Meth. Enzymol. 194, 3-21.
Treco and Lundblad (2001) Current Protocols in Molecular Biology Chapter 13:Unit 13.1.
Voth et al., (2003). YEAST, 20(11), 985-93.
Wu and Lichten (1994). Science 263, 515-518.
Zenvirth et al. (1997). Genes to Cells 2, 487-498.

The invention claimed is:

1. A method for improving a characteristic of interest of a yeast strain of industrial interest, comprising:
   a) transferring the yeast from a rich medium to a sporulation medium;
   b) incubating the yeast in the sporulation medium for a length of time sufficient to induce the formation of Spo11-dependent double-strand breaks;
   c) placing the yeast in contact with a source of carbon and nitrogen before the reductional chromosome segregation of the first meiotic division in order to obtain recombinant yeast undergoing recombination;
   d) collecting the recombinant yeast; and
   e) screening the recombinant yeast by measuring the characteristic of interest of the recombinant yeast and selecting recombinant yeast having the desired improvement of the characteristic of interest,
   repeating steps a) to d) or a) to e) at least once using one or more recombinant yeast collected in step d) or selected in step e); and
   wherein the recombinant yeast having the desired improvement of the characteristic of interest are non-genetically modified organisms.

2. The method according to claim 1, further comprising obtaining one or more recombinant yeast having the desired improvement of the characteristic of interest, from the screening or selection of step e).

3. The method according to claim 1, wherein the recombinant yeast collected in step d) are stored in yeast libraries before being screened or selected.

4. The method according to claim 1, wherein said yeast strain of industrial interest has a ploidy level greater than or equal to 2.

5. The method according to claim 1, wherein said yeast strain of industrial interest is a hybrid yeast.

6. The method according to claim 1, wherein said yeast strain of industrial interest is a diploid yeast or a diploid hybrid yeast.

7. The method according to claim 1, wherein said yeast strain of industrial interest is a sterile strain or a sterile hybrid strain.

8. The method according to claim 1, wherein said yeast strain of industrial interest is a sterile diploid hybrid strain.

9. The method according to claim 1, wherein the recombinant yeast present a plurality of recombination events per cell.

10. The method according to claim 9, wherein said recombination events induce a decrease in the level of heterozygosity.

11. The method according to claim 1, wherein the sporulation medium does not comprise a fermentable carbon source or nitrogen source.

12. The method according to claim 1, wherein the yeast are placed in contact with a source of carbon and nitrogen, before the reductional chromosome segregation of the first meiotic division, by transferring the yeast to a rich medium.

13. The method according to claim 1, wherein the characteristic of interest that is measured is selected from the group consisting of growth rate, thermotolerance, cryotolerance, pH sensitivity, fermentability, fermentation rate, resistance to ethanol, resistance to a particular compound present in a fermentation medium or excreted from a cell culture, cell morphology, flocculation, sensitivity to a particular molecule, efficiency of sporulation, aromatic profiles, nutritional requirements, resistance to drying, and fermentation of a particular sugar.

14. The method according to claim 13, wherein the characteristic of interest is resistance to a particular compound present in a fermentation medium or excreted from a cell culture.

15. The method according to claim 1, said method comprising repeating steps a) to d) at least once using one or more recombinant yeast collected in step d).

16. The method according to claim 1, said method comprising repeating steps a) to e) at least once using one or more recombinant yeast collected in selected in step e).

* * * * *

UNITED STATES PATENT AND TRADEMARK OFFICE
CERTIFICATE OF CORRECTION

Page 1 of 2

PATENT NO. : 10,844,367 B2
APPLICATION NO. : 14/647858
DATED : November 24, 2020
INVENTOR(S) : Alain Nicolas and Gianni Liti It is certified that error appears in the above-identified patent and that said Letters Patent is hereby corrected as shown below:

In the Specification

Column 5,
Line 5, "SK genetic" should read --SK1 genetic--.

Column 13,
Line 36, "Spo1-dependent" should read --Spo11-dependent--.

Column 15,
Line 3, "Spo1-dependent" should read --Spo11-dependent--.

Column 22,
Line 59, "(SK) were" should read --(SK1) were--.

Column 23,
Line 36, "AND1739(M)-AND174(D))" should read --AND1739(M)-AND1740(D))--.
Line 37, "AND172, Protocol for" should read --AND1702, Protocol 3 for--.
Line 41, "(RT3805)" should read --(ORT3805)--.

Column 24,
Line 14, "AND171," should read --AND1710,--.
Line 16, "AND171," should read --AND1710,--.

Column 25,
Line 26, "0RT7219" should read --ORT7219--.
Line 45, "average 1700" should read --average 17%--.

Column 26,
Line 42, "AND1709 (FIG. 1)," should read --AND1709 (FIG. 1B),--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

Column 27,
Line 40, "The ndt80 ndt80" should read --The *ndt80Δ/ndt80Δ*--.
Line 46, "FIGS. SA-C," should read --FIGS. 5A-C,--.

SEQUENCE LISTING

<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Forward primer ARG4

<400> SEQUENCE: 1
tactcattgg cagaatcccg                                       20

<210> SEQ ID NO 2
<211> LENGTH: 20
<212> TYPE: DNA
<213> ORGANISM: Artificial
<220> FEATURE:
<223> OTHER INFORMATION: Reverse primer ARG4

```
<400> SEQUENCE: 2
cgcttgagag gaagattagc                                          20
```